US012721800B2

(12) United States Patent
Margel et al.

(10) Patent No.: US 12,721,800 B2
(45) Date of Patent: Sep. 1, 2026

(54) PHOSPHONATES AND N-HALAMINES COMPOSITIONS FOR TARTAR REMOVAL

(71) Applicants: O.Y.M. INNOVATION LTD., Beit Herut (IL); BAR-ILAN UNIVERSITY, Ramat Gan (IL)

(72) Inventors: Shlomo Margel, Rehovot (IL); Hanna Steinmetz, Petah Tikva (IL); Chen Gelber, Netanya (IL); Yarden Goldstein, Herzlia (IL)

(73) Assignees: O.Y.M. INNOVATION LTD., Beit Herut (IL); BAR-ILAN UNIVERSITY, Ramat Gan (IL)

( * ) Notice: Subject to any disclaimer, the term of this patent is extended or adjusted under 35 U.S.C. 154(b) by 453 days.

(21) Appl. No.: 18/269,632

(22) PCT Filed: Jan. 3, 2022

(86) PCT No.: PCT/IL2022/050009

§ 371 (c)(1),
(2) Date: Jun. 26, 2023

(87) PCT Pub. No.: WO2022/149126

PCT Pub. Date: Jul. 14, 2022

(65) Prior Publication Data

US 2024/0091121 A1 Mar. 21, 2024

(30) Foreign Application Priority Data

Jan. 5, 2021 (IL) ........................................ 279966

(51) Int. Cl.

| | |
|---|---|
| ***A61K 8/55*** | (2006.01) |
| ***A61K 8/02*** | (2006.01) |
| ***A61K 8/11*** | (2006.01) |
| ***A61K 8/24*** | (2006.01) |
| ***A61K 8/25*** | (2006.01) |
| ***A61K 8/41*** | (2006.01) |
| ***A61K 8/58*** | (2006.01) |
| ***A61K 8/81*** | (2006.01) |
| ***A61K 8/88*** | (2006.01) |
| ***A61Q 11/00*** | (2006.01) |
| ***C07F 9/38*** | (2006.01) |

(52) U.S. Cl.

CPC .............. *A61K 8/55* (2013.01); *A61K 8/0241* (2013.01); *A61K 8/11* (2013.01); *A61K 8/24* (2013.01); *A61K 8/25* (2013.01); *A61K 8/41* (2013.01); *A61K 8/585* (2013.01); *A61K 8/8152* (2013.01); *A61K 8/8164* (2013.01); *A61K 8/88* (2013.01); *A61Q 11/00* (2013.01); *C07F 9/386* (2013.01); *A61K 2800/412* (2013.01); *A61K 2800/413* (2013.01); *A61K 2800/622* (2013.01); *A61K 2800/651* (2013.01); *A61K 2800/652* (2013.01); *A61K 2800/654* (2013.01)

(58) Field of Classification Search

None

See application file for complete search history.

(56) References Cited

U.S. PATENT DOCUMENTS

| | | | | |
|---|---|---|---|---|
| 3,678,154 | A | 7/1972 | Widder et al. | |
| 3,962,432 | A * | 6/1976 | Schmidt-Dunker | A61K 8/55 514/891 |
| 4,892,679 | A | 1/1990 | Blum et al. | |
| 4,892,724 | A * | 1/1990 | Amjad | A61K 8/8147 424/49 |
| 5,770,586 | A | 6/1998 | Ebetino et al. | |
| 9,884,880 | B2 | 2/2018 | Margel et al. | |
| 10,508,126 | B2 | 12/2019 | Margel et al. | |
| 10,849,729 | B2 | 12/2020 | Sagel et al. | |
| 2006/0233724 | A1 | 10/2006 | Yoshii et al. | |
| 2015/0153938 | A1 | 6/2015 | Muller et al. | |

FOREIGN PATENT DOCUMENTS

| | | | | |
|---|---|---|---|---|
| CA | 1008079 | A | 4/1977 | |
| CA | 1025705 | A | 2/1978 | |
| CN | 101181192 | A | 5/2008 | |
| DE | 102017010590 | | 5/2019 | |
| DE | 102017010590 | A1 * | 5/2019 | C22B 3/288 |
| GB | 1468144 | A | 3/1977 | |
| JP | S 49-048848 | A | 5/1985 | |
| WO | WO 1994/000102 | A1 | 1/1994 | |
| WO | WO 1995/008979 | A1 | 4/1995 | |
| WO | WO 2008/090527 | A1 | 7/2008 | |

OTHER PUBLICATIONS

Machine translation DE102017010590A1, May 16, 2019, pp. 1-15 (Year: 2019).*

Abraham et al. "μX-ray fluorescence analysis of traces and calcium phosphate phases on tooth-tartar interfaces using synchrotron radiation" Spectrochimica Acta Part B: Atomic Spectroscopy. Jul. 1, 2007;62(6-7):689-94.

Chen et al. "Synthesis and Characterization of NIR Fluorescent Polystyrene/Polystyrylbisphosphonate Core Shell Microspheres" Phosphorus, Sulfur, and Silicon and the Related Elements. Jun. 3, 2015;190(5-6):870-8.

Chen et al. "Thermal Behavior Study of Tri-Sodium Styrylbisphosphonate Using TGA/TGA-MS and 31P NMR" Phosphorus, Sulfur, and Silicon and the Related Elements. Jun. 3, 2015;190(5-6):905-10.

Gluz et al. "Engineering of new crosslinked near-infrared fluorescent polyethylene glycol bisphosphonate nanoparticles for bone targeting" Journal of Polymer Science Part A: Polymer Chemistry. Oct. 2013;51(20):4282-91.

(Continued)

*Primary Examiner* — Medhanit W Bahta
(74) *Attorney, Agent, or Firm* — Mark S. Cohen; PEARL COHEN LLP

(57) ABSTRACT

Provided herein are compositions and methods comprising phosphonates, N-halamines or combination thereof for dental care. Specifically, for removing tartar (calculus), including mature tartar.

24 Claims, 6 Drawing Sheets

(56) References Cited

OTHER PUBLICATIONS

Gluz et al. "Synthesis and characterization of new poly (ethylene glycol) bisphosphonate vinylic monomer and non-fluorescent and NIR-fluorescent bisphosphonate micrometer-sized particles" Polymer. Jan. 24, 2013;54(2):565-71.
Gluz et al. "New biodegradable bisphosphonate vinylic monomers and near infrared fluorescent nanoparticles for biomedical applications" Polymers for advanced technologies. May 2014;25(5):499-506.
Gutman et al. "Characterization and antibacterial properties of N-halamine-derivatized cross-linked polymethacrylamide nanoparticles" Biomaterials. Jun. 2014;35(19):5079-87.
Haham et al. "Engineering of Superparamagnetic Core-Shell Iron Oxide/N-Chloramine Nanoparticles for Water Purification" ACS applied materials & interfaces. Jul. 20, 2016;8(28):18488-95.
International Search Report for PCT Application No. PCT/IL2022/050009 dated Aug. 8, 2022.
Natan et al. "Killing mechanism of stable N-halamine cross-linked polymethacrylamide nanoparticles that selectively target bacteria" ACS nano. Feb. 24, 2015;9(2):1175-88.
Natan et al. "Engineering Irrigation Drippers with Rechargeable N-Halamine Nanoparticles for Antifouling Applications" ACS applied materials & interfaces. Jul. 3, 2019;11(26):23584-90.
Preoteasa et al. "Combined PIXE and optical microscopy characterization of calcium compounds in dental calculus" Nuclear Instruments and Methods in Physics Research Section B: Beam Interactions with Materials and Atoms. Jul. 1, 2021;498:39-47.
Rudnick-Glick et al. "Near IR fluorescent conjugated poly (ethylene glycol) bisphosphonate nanoparticles for in vivo bone targeting in a young mouse model" Journal of Nanobiotechnology. 2015;13.
Rudnick-Glick et al. Targeted drug delivery of near IR fluorescent doxorubicin-conjugated poly (ethylene glycol) bisphosphonate nanoparticles for diagnosis and therapy of primary and metastatic bone cancer in a mouse model. Journal of Nanobiotechnology. 2016;14.
Rudnick-Glick et al. "Doxorubicin-conjugated bisphosphonate nanoparticles for the therapy of osteosarcoma" JSM Nanotechnol Nanomed. 2014;1022(2).
Steinmetz et al. "Poly (styryl bisphosphonate) nanoparticles with a narrow size distribution: synthesis, characterization and antibacterial applications" European Polymer Journal. Jul. 1, 2019;116:65-73.
Steinmetz et al. "Engineering of new durable cross-linked poly (styryl bisphosphonate) thin coatings onto polypropylene films for biomedical applications" Applied Surface Science. Apr. 1, 2020;508:145171.
Tal et al. "Novel bisphosphonates near infrared fluorescent and non-fluorescent nanoparticles of narrow size distribution for bone targeting" Polymer. Dec. 6, 2017;132:188-92.
Tal et al. "Engineering of a New Bisphosphonate Monomer and Nanoparticles of Narrow Size Distribution for Antibacterial Applications" ACS Omega. Feb. 2, 2018;3(2):1458.
Marion D. Francis & William W. Briner, The effect of phosphanates on dental enamel in vitro and calculus formation in vivo Calc. Tiss. Res. vol. 11, 1-9 (1973).
Database Registry,2019 Year 06 / 06, RN 2325676-50-2, Retrieved from STNinternational [online] ; retrieved on Feb. 9, 2026.
Dyba, Marcin et al ., "1-Hydroxyalkane-1,1-diyldiphosphonates as potent chelating agents for metal ions. Potentiometric and spectroscopic studies of copper(II) co-ordination",Journal of the Chemical Society, Dalton Transactions,1996 Year, No. 6,p. 1119, DOI: 10.1039/DT9960001119.
Lalatonne, Y. et al ., "Superparamagnetic Bifunctional Bisphosphonates Nanoparticles: A Potential MRI Contrast Agent for Osteoporosis Therapy and Diagnostic",Journal of Osteoporosis,2010 year, vol. 2010,p. 1-7,DOI: 10.4061/2010/747852.
Teixeira, Ftima C. et al ., "Nafion phosphonic acid composite membranes for proton exchange membranes fuel cells",Applied Surface Science,vol. 487,2019 Year 09, p. 889-897,DOI: 10.1016/j.apsusc.2019.05.078.
Van Gelder, Joel M. et al ., "In Vitro and In Vivo Effects of Tetrakisphosphonates on Bone Resorption, Tumor Osteolysis, Ectopic Calcification, and acrophages",Journal of Pharmaceutical Sciences,1997 , 03, vol. 86,No. 3,p. 283-289, DOI: 10.1021/js960429h.

* cited by examiner before after before after before after

PHOSPHONATES AND N-HALAMINES COMPOSITIONS FOR TARTAR REMOVAL

CROSS-REFERENCE TO RELATED APPLICATIONS

This application is a National Phase Application of PCT International Application No. PCT/IL2022/050009, International Filing Date Jan. 3, 2022, claiming priority from Israeli Patent Application No. IL 279966, filed Jan. 5, 2021, which are hereby incorporated by reference.

FIELD OF THE INVENTION

Provided herein are compositions and methods comprising phosphonates, N-halamines or combination thereof for dental care. Specifically, for removing tartar (calculus).

BACKGROUND OF THE INVENTION

Dental Calculus (tartar), is a solid material due to plaque buildup that hardens (calcifies) on the teeth.

Dental plaque naturally grows on the tooth surface and forms part of the host defensive mouth of exogenous microorganisms by serving as a colonization barrier. This barrier effect is known as resistance to colonization. Plaques contain around 80% water and 20% solids. About half of the dry weight of the plaque is bacterial and salivary proteins. Approximately, 25% plaque dry weight is in the plaque matrix, in addition to its high protein concentration, carbohydrates, and lipids.

Dental Calculus (tartar) is a hardened surface and provides more surface area for plaque to adhere. More plaque can mean more periodontal diseases, halitosis and caries. Therefore, removing calculus is an important step to long-term oral health. Another downfall of tartar is its ability to absorb stains easily given its porous qualities.

Uncontrolled bacteria of dental plaque generate formation of oral biofilm located on teeth and subgingival surfaces. It may induce local inflammation (gingivitis) with further development of periodontal diseases. A variety of oral bacteria such as Streptococcus nutans and Porhyromonas gingivalis are involved in pathogenesis of dental carries and periodontitis. Very often bacterial infections are associated with candidiasi s (Candida albicans).

There are two types of dental calculus (tartar): (i) Supragingival tartar forms above the gumline. It's yellow or tan and is visible on a tooth's surface; and (ii) Subgingival tartar forms below the gumline in the sulcus (crevice) between the teeth and the gumline. It is typically not visible with the naked eye unless gum recession has already taken place.

Further there are two stages of dental calculus (tartar): (i) early (unmature) calculus (early tartar); and (ii) mature calculus (mature tartar). Early calculus (early tartar) refers to an early stage forming calculus which is mostly inorganic Brucite $CaHPO_4 \cdot 2H_2O$. Early calculus is softer in its nature therefore can be brushed off white dentifrice and toothbrush. Mature calculus (mature taratr) refers to a later stage of tartar forming calculus which contain at least one of in the intermediate phase octacalcium phosphate $Ca_4H(PO_4)_3 \cdot 2H_2O$, that further change to hydroxapetite $Ca_{10}(OH)_2(PO4)_6$ and/or whitlockite $Ca_9(PO_4)_6XPO_4$. The mature tartar is also known as hard tartar.

Early calculus is chalky spongy like calcified plaque that adhere to tooth surfaces. In its early stage the tartar is relatively soft and has a weaker bond strength to tooth surface. Further, early tartar is more prone to be disturbed by toothbrush strokes and by chemical—such as in ingredients in tartar control toothpastes. As early tartar is untreated it accumulates more calcified layers and becomes crystal hard and bonded hard to the tooth surface and is considered as mature tartar.

Once mature calculus is formed on the teeth, it can be removed only by a dental professional, regular brushing and flossing are not effective for removing it, whereas early-stage tartar more susceptible to tartar control dentifrice. Mature tartar is removed via a process known as debridement by a hand-held instrument or using an ultrasonic device to remove the tartar. Dental calculus should be removed periodically to maintain healthy teeth.

Today, a large range of products are marketed (mouth rinses, toothpastes, chewing gums, etc.) for removing tartar, labeled as 'Tartar Control' or ' Tartar Protection' however, there is no commercial product for removing mature calculus (mature tartar).

Numerous studies have shown that pyrophosphates are commonly used in the products for removing tartar, However, the inventors of this invention show (FIGS. 6-9) that pyrophosphonate does not remove mature tartar.

Bisphosphonates are non-hydroly sable pyrophosphate analogs with high affinity to calcium ions due to their ability to create bidentate and/or tridentate chelates with calcium ions. Consequently, bisphosphonates lead to strong interactions with dentin, enamel and bones. Up to date, the wide clinical use of approved bisphosphonates is for treatment of bone diseases associated with bone fragmentation, such as bone malignancies, osteoporosis, Paget's disease, etc. In addition to their strong affinity to calcium ion in the bone mineral, bisphosphonates (especially those bearing OH) accelerate osteoblasts action, while strongly inhibiting osteoclasts, thus contributing to enhanced bone formation.

N-halamines are a class of compounds, containing one or more nitrogen-halogen covalent bonds, and are known for their antimicrobial activity. N-halamines possess several advantages including long-term stability in aqueous solutions, specificity, low toxicity, relatively inexpensive, and the capacity for efficient regeneration to cany halogens. The latter is a unique property that distinguishes N-halamines from other antimicrobials.

Periimplantitis diseases are inflammatory process affecting the soft and hard tissues around an implant that results in loss of supporting bone. Similar to a natural tooth, bacteria can build up on the base of the implant, below the gum line. Over time, the bacteria irritate the gum tissue, causing it to become inflamed, damaging the tissue and if not caught early, causing the bone structure below the implant to deteriorate.

Periodontal disease, also known as gum disease, is a set of inflammatory conditions affecting the tissues surrounding the teeth. Generally due to bacteria in the mouth infecting the tissue around the teeth Provided herein is an efficient use of polyphosphonate (bisphosphonates, tetra phosphonates, polymerized phosphonate) and/or N-halamines for removing calculus (tartar), especially removing mature calculus (mature tartar) without the need of dental professional. Further, the composition of this invention also treats and prevents dental caries or treats periimplantitis or periodontal diseases.

SUMMARY OF THE INVENTION

In some embodiments, this invention provides a dental care composition comprising at least one poly-phosphonate or salt thereof in an amount of 0.05%-30% by weight of said composition; and a pharmaceutically acceptable carrier; for use in removing mature tartar from the tooth surface of a subject. In another embodiment, the dental care composition further comprises N-halamine.

In one embodiment, the dental care composition of this invention comprises a poly-phosphonate or salt thereof, wherein the poly-phosphonate comprises a bisphosphonate compound, a tetra-phosphonate compound, a polymerized phosphonate, a polymerized bisphosphonate, or a polymerized tetra-phosphonate.

In one embodiment, the poly-phosphonate is in a form of a nanoparticle or microparticle.

In one embodiment, the dental care composition of this invention comprises a poly-phosphonate represented by the following structure or salt thereof:

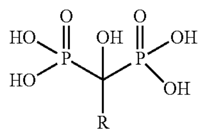

wherein R is hydrogen, substituted or unsubstituted alkyl, substituted or unsubstituted aryl;

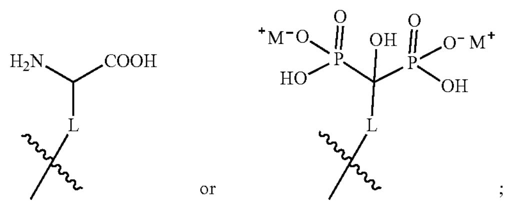

or ;

and

L is alkyl, alkylaryl, alkynyl, aryl, alkyl ether, alkyl thioether, alkyl amide, alkyl amine, or an amino side chain; wherein the side chain of the amino acid is attached to the carbon; wherein said alkyl, aryl, alkylaryl, alkynyl, alkyl ether, alkyl thioether, alkyl amide, alkyl amine, or an amino side chain are each substituted or unsubstituted.

In another embodiment, the poly-phosphonate is a bisphosphonate compound represented by the following structure (γ-Glu-BP) or salt thereof:

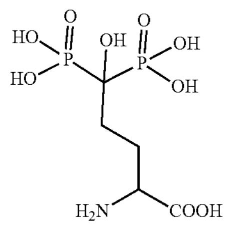 [SMILES: NC(CCC(O)(P(=O)(O)O)P(=O)(O)O)C(=O)O]

In another embodiment, the poly-phosphonate is a polymerized bis-phosphonate, comprising a bispohophonate monomer represented by the following structure or salt thereof:

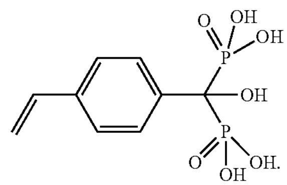 [SMILES: C=Cc1ccc(C(O)(P(=O)(O)O)P(=O)(O)O)cc1]

In another embodiment, the poly-phosphonate is a tetra phosphonate compound represented by the following structure or salt thereof:

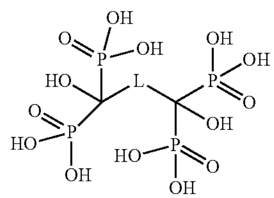

wherein,

L is alkyl, alkylaryl, alkynyl, aryl, alkyl ether, alkyl thioether, alkyl amide, alkyl amine, or an amino side chain; wherein the side chain of the amino acid is attached to the carbon; and wherein said alkyl, aryl, alkylaryl, alkynyl, alkyl ether, alkyl thioether, alkyl amide, alkyl amine, or an amino side chain are substituted or unsubstituted.

In another embodiment, the tetra phosphonate compounds is represented by the following structure: (succinyl tetra phosphonate (SUTP) or alkali salt thereof; or a malonic tetra phosphonate or alkali salt thereof):

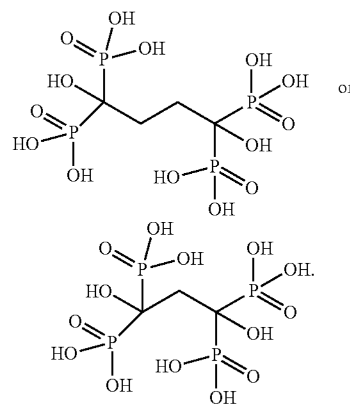

or

In another embodiment, the dental care composition further comprises N-halamine compound, N-halamine based polymer, or N-halamine based particle in an amount of between 0.1%-10% by weight of said composition.

In some embodiments, provided herein is a dental care composition comprising at least one N-halamine compound, N-halamine based polymer, or N-halamine based particle in an amount of 0.1%-10% by weight of said composition; and a pharmaceutically acceptable carrier for use in removing tartar from the tooth surface of a subject. In another embodiment, the tartar is a mature tartar.

In another embodiment, the N-halamine compound comprises a halogenated primary amine, a halogenated secondary amine, a halogenated amide or a halogenated urea.

In another embodiment, the N-halamine based particle is in a form of a core/shell silica halamine-urea particles represented by the following structure:

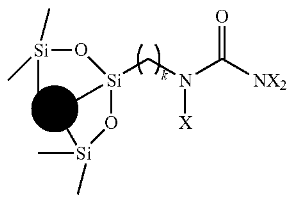

wherein X is independently a halide and k is between 1-10.

In another embodiment, the N-halamine polymer is represented by the following structures:

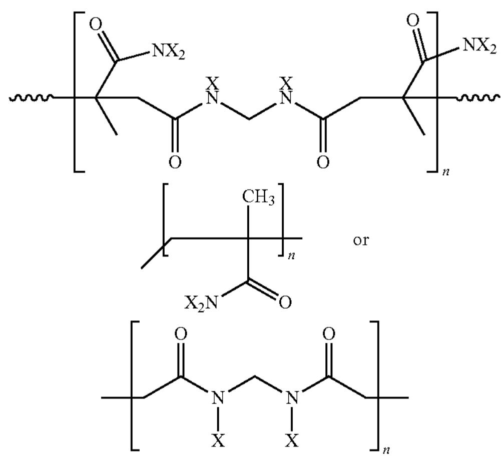

or wherein X is independently a halide and n is between 2-100.

In some embodiment, provided herein, a dental care composition comprising at least one N-halamine based polymer or N-halamine based particle in an amount of 0.1-10% by weight of said composition, and a pharmaceutically acceptable carrier, wherein the N-halamine based polymer is represented by the following structures:

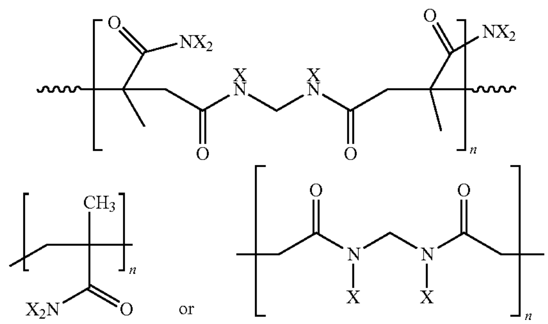

or and the N-halamine based particle is in a form of a core/shell silica halamine-urea particles represented by the following structure:

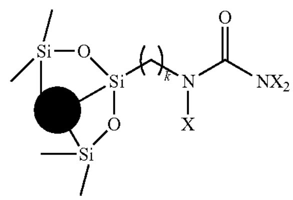

wherein X is independently a halide and k is between 1-10, for use in treating or preventing dental caries and/or for treating or preventing periimplantitis or periodontal diseases.

In another embodiment, the dental care composition comprises N-halamine as provided herein and a poly-phosphonate or salt thereof as provided herein.

In one embodiment, the dental care composition provided herein is formulated as a solution, a paste, gel, spray, foam, toothpaste, mouthwash, dental tray, tooth filler, dentifrices, dissolvable or non-dissolvable thin film, dissolvable or non-dissolvable dental strip, as an edible film forming agent, drops, chewing gum, or as a coating on dental implants.

In one embodiment, this invention provides a succinyl tetra phosphonate compound represented by the following structure or alkali salt thereof:

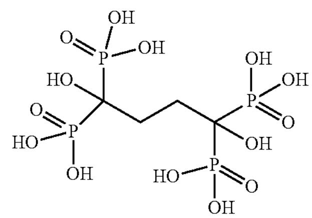 [SMILES: O=P(O)(O)C(O)(CCC(O)(P(=O)(O)O)P(=O)(O)O)P(=O)(O)O]

or a malonyl tetra phosphonate compound represented by the following structure or alkali salt thereof:

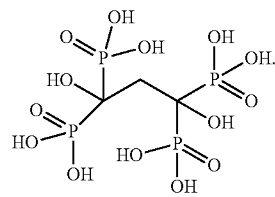 [SMILES: O=P(O)(O)C(O)(CC(O)(P(=O)(O)O)P(=O)(O)O)P(=O)(O)O]

In some embodiments, this invention provides a dental care composition comprising a succinyl or a malonyl tetra phosphonate compound or alkali salt thereof of this invention and a pharmaceutically acceptable carrier.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 1B: after treatment); and with 1 mg/mL of SUTP (FIG. 1C: before treatment; FIG. 1D after treatment)

FIG. 5B: after treatment); and with 2 mM of PMAA-Cl (FIG. 5C: before treatment; FIG. 5D after treatment).

Figure 1A:
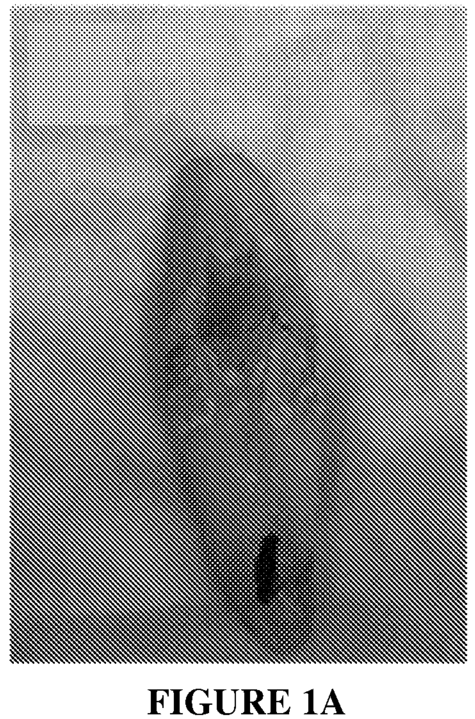
FIGS. 1A-1D presents pictures of teeth with mature tartar before and after treatment with 10 mg/mL of succinyl tetra phosphonate, SUTP (FIG. 1A: before treatment.
Figure 1A:
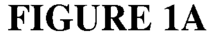

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Compositions

In some embodiments, this invention provides a dental care composition comprising at least one poly-phosphonate or salt thereof, N-halamine or combination thereof; or a co-polymer comprising a phosphonate backbone and a N-halamine backbone; and a pharmaceutically acceptable carrier.

In some embodiments, this invention provides a dental care composition comprising at least one poly-phosphonate or salt thereof, N-halamine compound, N-halamine based polymer, N-halamine based particle or any combination thereof; or a co-polymer comprising a phosphonate backbone and a N-halamine backbone; and a pharmaceutically acceptable carrier.

In some embodiments, this invention provides a dental care composition comprising at least one poly-phosphonate or salt thereof, and a pharmaceutically acceptable carrier. In another embodiment, the poly-phosphonate comprises a bisphosphonate compound, a tetra-phosphonate compound, a polymerized phosphonate, a polymerized bis-phosphonate, or a polymerized tetra-phosphonate.

In some embodiments, this invention provides a dental care composition comprising tetra-phosphates compound or alkali salt thereof and bisphosphonate compound or salt thereof.

In some embodiments, this invention provides a dental care composition comprising tetra-phosphates compound or alkali salt thereof and polymerized bisphosphonate or salt thereof.

In some embodiments, this invention provides a dental care composition comprising at least one poly-phosphonate or salt thereof and a pharmaceutically acceptable carrier.

In some embodiments, this invention provides a dental care composition comprising at least one N-halamine compound, N-halamine based polymer, N-halamine based particle, or combination thereof, and a pharmaceutically acceptable carrier.

In some embodiments, this invention provides a dental care composition comprising at least one poly-phosphonate and at least one of N-halamine compound, N-halamine based polymer, N-halamine based particle; and a pharmaceutically acceptable carrier.

This invention provides a dental care composition comprising co-polymer comprising a phosphonate backbone and a N-halamine backbone, and a pharmaceutically acceptable carrier.

In some embodiments, this invention provides a dental care composition comprising at least one poly-phosphonate, N-halamine compound, N-halamine based polymer, N-halamine based particle, or combination thereof; or a co-polymer comprising a phosphonate backbone and a N-halamine backbone; and a pharmaceutically acceptable carrier for use in removing tartar from the tooth surface of a subject. In another embodiment, the tartar is early and mature tartar. In another embodiment, the tartar is mature tartar.

In some embodiments, this invention provides a dental care composition comprising at least one poly-phosphonate or salt thereof, N-halamine compound, N-halamine based polymer, N-halamine based particle; or a co-polymer comprising a phosphonate backbone and a N-halamine backbone; and a pharmaceutically acceptable carrier for use in removing mature tartar from the tooth surface of a subject; wherein the poly-phosphonate comprises a bisphosphonate compound, a tetra-phosphonate compound, a polymerized phosphonate, a polymerized bis-phosphonate, or a polymerized tetra-phosphonate.

In some embodiments, this invention provides a dental care composition comprising at least one poly-phosphonate or salt thereof, in an amount of 0.05%-30% by weight of said composition; and a pharmaceutically acceptable carrier; for use in removing mature tartar from the tooth surface of a subject. In one embodiment, the poly-phosphonate comprises a bisphosphonate compound, a tetra-phosphonate compound, a polymerized phosphonate, a polymerized bisphosphonate, or a polymerized tetra-phosphonate.

In some embodiments, this invention provides a dental care composition comprising at least one poly-phosphonate or salt thereof, in an amount of 0.05%-10% by weight of said composition; and a pharmaceutically acceptable carrier; for use in removing mature tartar from the tooth surface of a subject. In one embodiment, the poly-phosphonate comprises a bisphosphonate compound, a tetra-phosphonate compound, a polymerized phosphonate, a polymerized bisphosphonate, or a polymerized tetra-phosphonate.

In another embodiment, the poly-phosphonate or salt thereof provided herein is in a form of nanoparticle or microparticle.

In some embodiments, this invention provides a dental care composition comprising at least one N-halamine compound, N-halamine based polymer, or N-halamine based particle is in an amount of 0.1%-10% by weight of said composition; and a pharmaceutically acceptable carrier for use in removing tartar from the tooth surface of a subject.

In some embodiments, this invention provides a dental care composition comprising at least one N-halamine compound, N-halamine based polymer, or N-halamine based particle or combination thereof; or combination of at least one poly-phosphonate and N-halamine compound, N-halamine based polymer, or N-halamine based particle; or a co-polymer comprising a phosphonate backbone and a N-halamine backbone; and a pharmaceutically acceptable carrier for use in removing tartar from the tooth surface of a subject. In another embodiment, the tartar is mature tartar.

This invention provides a dental care composition comprising at least one N-halamine compound, N-halamine based polymer, or N-halamine based particle or combination thereof; or combination of at least one poly-phosphonate compound and N-halamine compound, N-halamine based polymer, or N-halamine based particle; or a co-polymer comprising a phosphonate backbone and a N-halamine backbone; and a pharmaceutically acceptable carrier for use in treating or preventing dental caries. This invention provides a dental care composition comprising at least one N-halamine compound, N-halamine based polymer, or N-halamine based particle or combination thereof; or combination of at least one poly-phosphonate compound and N-halamine compound, N-halamine based polymer, or N-halamine based particle; or a co-polymer comprising a phosphonate backbone and a N-halamine backbone; and a pharmaceutically acceptable carrier for use in for treating or preventing periimplantitis.

In some embodiments, this invention provides a dental care composition comprising at least one N-halamine compound, N-halamine based polymer, or N-halamine based particle or combination thereof; or combination of at least one poly-phosphonate compound and N-halamine compound, N-halamine based polymer, or N-halamine based particle N-halamine based polymer, N-halamine based particle or a co-polymer comprising a phosphonate backbone and a N-halamine backbone; and a pharmaceutically acceptable carrier for use in for treating or preventing periodontal disease.

In some embodiments, this invention provides a dental care composition comprising at least one poly-phosphonate or salt thereof, and a pharmaceutically acceptable carrier for use in (i) removing tartar (calculus) from the tooth surface of a subject; or (ii) removing mature tartar (mature calculus) from the tooth surface of a subject.

In another embodiment, the dental care composition comprising at least one poly-phosphonate or salt thereof, and a pharmaceutically acceptable carrier for use in removing mature tartar (mature calculus) from the tooth surface of a subject.

In another embodiment, the dental care composition comprising at least one poly-phosphonate or salt thereof, and a pharmaceutically acceptable carrier for use in removing octacalcium phosphate $Ca_4H(PO_4)_3 \cdot 2H_2O$, hydroxapetite $Ca_{10}(OH)_2(PO_4)_6$, whitlockite $Ca_9(PO_4)_6XPO_4$ or any combination thereof from the tooth surface of a subject. In another embodiment, the dental composition further comprises N-halamine compound, N-halamine based polymer, N-halamine based particle, or combination thereof.

In some embodiments, this invention provides a dental care composition comprising tetra-phosphates compound or alkali salt thereof and bisphosphonate compound or salt thereof, and a pharmaceutically acceptable carrier for use in removing mature tartar (mature calculus) from the tooth surface of a subject.

In some embodiments, this invention provides a dental care composition comprising tetra-phosphates compound or alkali salt thereof and polymerized bisphosphonate or salt thereof, and a pharmaceutically acceptable carrier for use in removing mature tartar (mature calculus) from the tooth surface of a subject.

In some embodiments, this invention provides a dental care composition comprising N-halamine compound, N-halamine based polymer, N-halamine based particle, or combination thereof, and a pharmaceutically acceptable carrier for use in (i) removing tartar from the tooth surface of a subject; (ii) removing mature tartar (mature calculus) from the tooth surface of a subject; (iii) treating or preventing dental caries; (iv) treating or preventing periimplantitis; or (v) treating or preventing periodontal. Each represents a separate embodiment of this invention. In another embodiment, the dental composition further comprises poly-phosphonate.

In some embodiments, this invention provides a dental care composition comprising N-halamine, and poly-phosphonate or salt thereof; and a pharmaceutically acceptable carrier for use in (i) removing tartar from the tooth surface of a subject; (ii) removing mature tartar (mature calculus) from the tooth surface of a subject; (iv) treating or preventing dental caries; (v) treating or preventing periimplantitis; or (vi) treating or preventing periodontal; Each represents a separate embodiment of this invention.

In some embodiments, this invention provides a dental care composition comprising co-polymer comprising a phosphonate backbone and a N-halamine backbone; and a pharmaceutically acceptable carrier for use in (i) removing tartar from the tooth surface of a subject; (ii) removing mature tartar (mature calculus) from the tooth surface of a subject; (iii) treating or preventing dental caries; (iv) treating or preventing periimplantitis; or (v) treating or preventing periodontal; Each represents a separate embodiment of this invention.

In some embodiments, this invention provides a dental care composition comprising at least one poly-phosphonate or salt thereof, N-halamine, or combination thereof or combination thereof; or a co-polymer comprising a phosphonate backbone and a N-halamine backbone; and a pharmaceutically acceptable carrier for use in (i) removing tartar from the tooth surface of a subject; (ii) removing mature tartar (mature calculus) from the tooth surface of a subject; (iii) treating or preventing dental caries; (iv) treating or preventing periimplantitis; or (v) treating or preventing periodontal. Each represents a separate embodiment of this invention.

In some embodiments, this invention provides a dental care composition comprising N-halamine compound, N-halamine based polymer, N-halamine based particle, or combination thereof, and a pharmaceutically acceptable carrier for use in (i) removing tartar from the tooth surface of a subject; (ii) removing mature tartar (mature calculus) from the tooth surface of a subject; (iii) treating or preventing dental caries; (iv) treating or preventing periimplantitis; or (v) treating or preventing periodontal. Each represents a separate embodiment of this invention. In another embodiment, the dental composition further comprises poly-phosphonate.

In some embodiments, this invention provides a dental care composition comprising N-halamine compound, N-halamine based polymer, N-halamine based particle, or combination thereof, and a pharmaceutically acceptable carrier for use in treating or preventing periimplantitis or treating or preventing periodontal. Each represents a separate embodiment of this invention. In another embodiment, the dental composition further comprises poly-phosphonate or salt thereof.

In some embodiments, this invention provides a dental care composition comprising N-halamine based polymer, N-halamine based particle, or combination thereof, and a pharmaceutically acceptable carrier wherein the N-halamine based polymer is represented by the following structures:

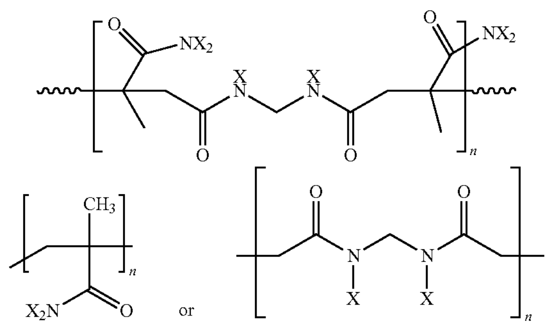

or

N-halamine based particle is in a form of a core/shell silica halamine-urea particles represented by the following structure:

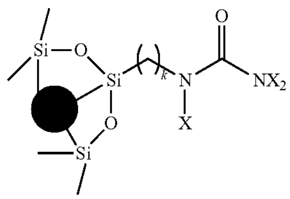

wherein X is a halide and k is between 1-10, for use in (i) removing tartar from the tooth surface of a subject; (ii) removing mature tartar (mature calculus) from the tooth surface of a subject; (iii) treating or preventing dental caries; (iv) treating or preventing periimplantitis; or (v) treating or preventing periodontal. Each represents a separate embodiment of this invention. In another embodiment, the dental composition further comprises poly-phosphonate or salt thereof.

In some embodiments, the dental care composition of this invention is for use in removing mature tartar from the tooth surface. In some embodiment, the dental care composition of this invention is for use in removing or decomposing octacalcium phosphate $Ca_4H(PO_4)_3 \cdot 2H_2O$ from the tooth surface. In some embodiment, the dental care composition of this invention is for use in removing or decomposing hydroxapetite $Ca_{10}(OH)_2(PO_4)_6$ and/or whitlockite $Ca_9(PO_4)_6XPO_4$.

In some embodiments, the removal of tartar with the dental care composition of this invention refers to a removal of supragingival tartar. In some embodiment, the removal of tartar with the dental care composition of this invention refers to a removal of subgingival tartar.

In some embodiments, the removal of mature tartar with the dental care composition of this invention refers to a removal of supragingival mature tartar. In some embodiment, the removal of mature tartar with the dental care composition of this invention refers to a removal of subgingival mature tartar.

The term "periodontal diseases" as used herein is also known as gum disease, is a set of inflammatory conditions affecting the tissues surrounding the teeth. Generally due to bacteria in the mouth infecting the tissue around the teeth. Periodontal diseases also include gingivitis or periodontitis.

In one embodiment, periimplantitis diseases are inflammatory conditions affecting the soft and hard gum tissues around dental implants. Similar to a natural tooth, bacteria can build up on the base of the implant, below the gum line. Over time, the bacteria irritate the gum tissue, causing it to become inflamed, damaging the tissue and if not caught early, causing the bone structure below the implant to deteriorate.

In another embodiment the composition and method of use thereof provided herein comprises between 0.01%-10% by weight poly-phosphonate or salt thereof. In another embodiment, the composition comprises between 0.05%-30% by weight poly-phosphonate. In another embodiment, the composition comprises between 0.05%-60% by weight poly-phosphonate or salt thereof. In another embodiment, the composition comprises between 0.05%-2% by weight poly-phosphonate or salt thereof. In another embodiment, the composition comprises between 0.05%-0.5% by weight poly-phosphonate. In another embodiment, the composition comprises between 0.1%-0.5% by weight poly-phosphonate or salt thereof. In another embodiment, the composition comprises between 0.1%-1% by weight poly-phosphonate or salt thereof. In another embodiment, the composition comprises between 0.1-0.2% by weight poly-phosphonate. In another embodiment, the composition comprises between 0.1-0.3% by weight poly-phosphonate or salt thereof. In another embodiment, the composition comprises between 0.1-0.4% by weight poly-phosphonate or salt thereof. In another embodiment, the composition comprises between 0.1-0.6% by weight poly-phosphonate or salt thereof. In another embodiment, the composition comprises between 0.1-0.7% by weight poly-phosphonate or salt thereof. In another embodiment, the composition comprises between 0.1-0.8% by weight poly-phosphonate or salt thereof. In another embodiment, the composition comprises between 0.1-0.9% by weight poly-phosphonate or salt thereof. In another embodiment, the composition comprises between 0.05-0.2% by weight poly-phosphonate or salt thereof. In another embodiment, the composition comprises between 0.05-0.3% by weight poly-phosphonate or salt thereof. In another embodiment, the composition comprises between 0.05-0.4% by weight poly-phosphonate or salt thereof. In another embodiment, the composition comprises between 0.05-0.6% by weight poly-phosphonate or salt thereof. In another embodiment, the composition comprises between 0.05-0.7% by weight poly-phosphonate or salt thereof. In another embodiment, the composition comprises between 0.05-0.8% by weight poly-phosphonate or salt thereof. In another embodiment, the composition comprises between 0.05-0.9% by weight poly-phosphonate or salt thereof. In another embodiment, the composition comprises between 1%-3% by weight poly-phosphonate or salt thereof. In another embodiment, the composition comprises between 1%-5% by weight poly-phosphonate or salt thereof. In another embodiment, the composition comprises between 0.05%-1.5% by weight poly-phosphonate or salt thereof. In another embodiment, the composition comprises between 0.1%-1.5% by weight poly-phosphonate or salt thereof. In another embodiment, the composition comprises between 3%-10% by weight poly-phosphonate or salt thereof. In another embodiment, the composition comprises between 1%-7.5% by weight poly-phosphonate. In another embodiment, the composition comprises between 2%-5% by weight poly-phosphonate or salt thereof. In another embodiment, the composition comprises between 1%-5% by weight poly-phosphonate or salt thereof. In another embodiment, the composition comprises between 4%-8% by weight poly-phosphonate or salt thereof. In another embodiment, the composition comprises between 3%-10% by weight poly-phosphonate or salt thereof. In another embodiment, the composition comprises between 5%-10% by weight poly-phosphonate or salt thereof. In another embodiment, the composition comprises between 0.5-10% by weight poly-phosphonate or salt thereof. In another embodiment, the composition comprises between 0.05%-7.5% by weight poly-phosphonate. In another embodiment, the composition comprises between 0.05%-10% by weight poly-phosphonate. In another embodiment, the composition comprises between 0.05%-20% by weight poly-phosphonate. In another embodiment, the composition comprises between 0.05%-25% by weight poly-phosphonate. In another embodiment, the composition comprises between 1%-20% by weight poly-phosphonate or salt thereof. In another embodiment, the composition comprises between 2%-10% by weight poly-phosphonate. In another embodiment, the composition comprises between 2%-20% by weight poly-phosphonate. In another embodiment, the composition comprises between 5%-30% by weight poly-phosphonate or salt thereof. In another embodiment, the composition comprises between 10%-12% by weight poly-phosphonate or salt thereof. In another embodiment, the composition comprises between 15-20% by weight poly-phosphonate or salt thereof. In another embodiment, the composition comprises between 12-20% by weight poly-phosphonate or salt thereof. In another embodiment, the composition comprises between 20-30% by weight poly-phosphonate or salt thereof. In another embodiment, the composition comprises between 30%-40% by weight poly-phosphonate or salt thereof. In another embodiment, the composition comprises between 40%-50% by weight poly-phosphonate or salt thereof. In another embodiment, the composition comprises 0.01%, 0.02%, 0.03%, 0.0.4%, 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10.0%, 11%, 11.5%, 12%, 12.5% 13%, 13.5% 14%, 14.5% 15%, 15.5% 16%, 16.5%, 17%, 17.5%, 18%, 18.5% 19%, 19.5% 20%, 21%, 22%, 23%, 24%, 25%, 26%, 27%, 28%, 29%, 30%, 35%, 40%, 45%, 50%, 55%, 60% by weight poly-phosphonate or salt thereof or any range thereof. Each represents a separate embodiment of this invention.

In another embodiment, the composition comprises between 0.1%-10% by weight N-halamine compound, N-halamine based polymer, or N-halamine based particle. In another embodiment, the composition comprises between 0.1%-2% by weight N-halamine compound, N-halamine based polymer, or N-halamine based particle. In another embodiment, the composition comprises between 0.5%-10% by weight N-halamine compound, N-halamine based polymer, or N-halamine based particle. In another embodiment, the composition comprises between 0.5%-2% by weight N-halamine compound, N-halamine based polymer, or N-halamine based particle. In another embodiment, the composition comprises between 0.1%-0.5% by weight N-halamine compound, N-halamine based polymer, or N-halamine based particle. In another embodiment, the composition comprises between 0.1%-1% by weight N-halamine compound, N-halamine based polymer, or N-halamine based particle. In another embodiment, the composition comprises between 1%-3% by weight N-halamine compound, N-halamine based polymer, or N-halamine based particle. In another embodiment, the composition comprises between 1%-5% by weight N-halamine compound, N-halamine based polymer, or N-halamine based particle. In another embodiment, the composition comprises between 0.1%-1.5% by weight N-halamine compound, N-halamine based polymer, or N-halamine based particle. In another embodiment, the composition comprises between 0.1%-1.5% by weight N-halamine compound, N-halamine based polymer, or N-halamine based particle.

In another embodiment, the composition comprises between 2%-5% by weight N-halamine compound, N-halamine based polymer, or N-halamine based particle. In another embodiment, the composition comprises between 4%-8% by weight N-halamine compound, N-halamine based polymer, or N-halamine based particle. In another embodiment, the composition comprises between 3%-10% by weight N-halamine compound, N-halamine based polymer, or N-halamine based particle. In another embodiment, the composition comprises between 5%-10% by weight N-halamine compound, N-halamine based polymer, or N-halamine based particle. In another embodiment, the composition comprises 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10.0% by weight N-halamine compound, N-halamine based polymer, or N-halamine based particle. Each represents a separate embodiment of this invention.

In another embodiment, the composition of this invention comprises 0.05%-30% w/w of poly-phosphnate or salt thereof and 0.01%-10% w/w N-halamine compound, N-halamine based polymer, or N-halamine based particle.

In some embodiment, the dental care composition comprising poly-phosphonate, and N-halamine compound, N-halamine based polymer, or N-halamine based particle, wherein the amount of the N-halamine compound, N-halamine based polymer, or N-halamine based particle is between 0.1%-10% by weight of said composition.

The term "tartar" or "calculus" or "dental calculus" mean, partially mineralized deposits on dental surfaces formed by the maturation of plaque. Tartar is a deposit of inorganic salts composed primary of calcium carbonate and phosphate mixed with bacteria food debris and desquamated epithelial cells.

The term "mature calculus", "mature tartar" means a later stage of forming calculus which contain at least one of octacalcium phosphate $Ca_4H(PO_4)_3 \cdot 2H_2O$, hydroxapetite $Ca_{10}(OH)_2(PO4)_6$ and/or whitlockite $Ca_9(PO_4)_6XPO_4$. In another embodiment, the mature tartar also known as hard tartar. In another embodiment, the mature tartar refers to tartar that needs to be removed via a process known as debridement by a hand-held instruments or using an ultrasonic device to remove the tartar.

The compositions of this invention are used for removing or decomposing calculus or tartar. In one embodiment, the compositions of this invention are used for removing mature calculus (mature tartar). The composition can be applied to the teeth by any known method. The compositions provided herein are formulates as dentifrices (including toothpastes), gels, mouthwashes, dissolvable or non-dissolvable thin films, dissolvable or non-dissolvable dental strips, as an edible film forming agent, as drops and chewing gum, spray, tooth filer, dental tray, solution, paste, foam, toothpaste, or tooth filler.

In another embodiment, the composition is formulated as a dragee, Lozenge, dissolvable lozenge, drops or a chewing gum. In another embodiment, the composition of this invention is used as coating for dental implants.

In another embodiment, the composition of this invention, is formulated in toothpaste, oral gel, poultice (e.g., dental dressing) paste, mouth wash, spray, dentifrice, toothpowder, mouthrinse, chewing gum, lozenge, or impregnated floss or brushes, tooth hardener. The instant compositions may also be presented in dissolvable and non-dissolvable films. In other embodiments, the composition of this invention is a solution, paste, gel, mouth wash or a cream.

In some embodiments the poly-phosphonate or salt thereof, the N-halamine compound, N-halamine based polymer, N-halamine particle or the co-polymer comprising a phosphonate backbone and a N-halamine backbone are referred herein as a calculus removal agent. In other embodiment, the calculus removal agent of this invention is a particle. In other embodiment, the calculus removal agent of this invention is encapsulated. In other embodiment, the calculus removal agent of this invention is polymerized.

Poly-Phosphonate

The term "poly-phosphonate" refers herein to bisphoshonate or salt thereof, triphosphonate or salt thereof, tetraphosphonates or salt thereof, polymerized bisphoshonate or salt thereof, polymerized triphosphonate or salt thereof, polymerized tetraphosphonates or salt thereof or more.

In another embodiment, the dental care composition of this invention comprises a poly-phosphonate, wherein the poly-phosphonate comprises a bisphosphonate compound, a tetra-phosphonate compound, a polymerized phosphonate, or a polymerized bisphosphonate, or a polymerized tetraphosphonate. In some embodiment, the poly-phosphonate compound provided herein is a nanoparticle or microparticle.

In some embodiments, the poly-phosphonate within the dental care composition of this invention is represented by the structure of formula I or salt thereof:

(I)

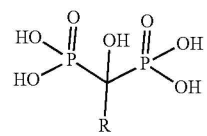

wherein

R is hydrogen, substituted or unsubstituted alkyl, substituted or unsubstituted aryl,

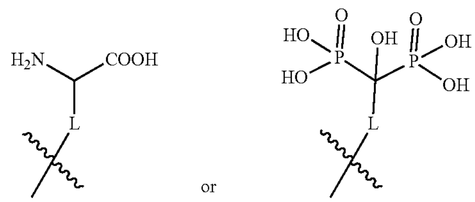

or ;

L is alkyl, alkylaryl, alkynyl, aryl, alkyl ether, alkyl thioether, alkyl amide, alkyl amine, or an amino side chain; wherein the side chain of the amino acid is attached to the carbon (C—OH); and wherein said alkyl, alkylaryl, alkynyl, aryl, alkyl ether, alkyl thioether, alkyl amide, alkyl amine, or an amino side chain are each substituted or unsubstituted.

In other embodiments, the poly-phosphonate is a bisphosphonate compound within the composition of this invention is represented by the following structure (γ-Glu-BP) or salt thereof:

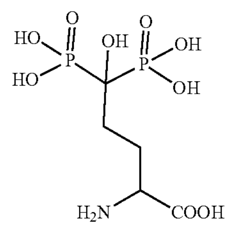

In some embodiments, the poly-phosphonate within the dental care composition of this invention comprises a polymerized bis-phosphonate.

In some embodiments, the poly-phosphonate is a polymerized bis-phosphonate, based on bispohophnate monomer represented by the following structure or alkali salt thereof

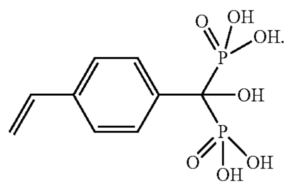 [SMILES: C=Cc1ccc(C(O)(P(=O)(O)O)P(=O)(O)O)cc1]

In some embodiments, the poly-phosphonate within the dental care composition of this invention comprises a tetra-phosphonate compound or alkali salt thereof.

In other embodiments, the tetra-phosphonate compound is represented by the following structure:

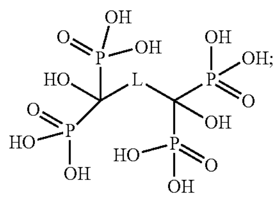

or salt thereof wherein,

L is alkyl, alkylaryl, alkynyl, aryl, alkyl ether, alkyl thioether, alkyl amide, alkyl amine, or an amino side chain; wherein the side chain of the amino acid is attached to the carbon; and wherein said alkyl, alkylaryl, alkynyl, aryl, alkyl ether, alkyl thioether, alkyl amide, alkyl amine, or an amino side chain are substituted or unsubstituted.

In some embodiments, L of the poly-phosphonate of this invention is alkyl, aryl, alkylaryl, alkynyl, alkyl ether, alkyl thioether, alkyl amide, alkyl amine, or an amino side chain; wherein the side chain of the amino acid is attached to the carbon. In another embodiment, L is substituted or unsubstituted alkyl. In another embodiment, L is unsubstituted alkyl. In another embodiment, L is substituted alkyl. In another embodiment, L is substituted or unsubstituted C2-C5 alkyl. In another embodiment, L is unsubstituted C2-C5 alkyl. In another embodiment, L is substituted C2-05 alkyl. In another embodiment, L is substituted or unsubstituted alkylaryl. In another embodiment, L is substituted or unsubstituted alkynyl. In another embodiment, L is substituted or unsubstituted aryl. In another embodiment, L is substituted or unsubstituted alkyl ether. In another embodiment, L is substituted or unsubstituted alkyl thioether. In another embodiment, L is substituted or unsubstituted alkyl amide. In another embodiment, L is substituted or unsubstituted alkyl amine.

In another embodiment, L of formula I or of the bisphosphonate or tetraphosphonate compounds provided herein is substituted or unsubstituted C1-C5 alkyl. In another embodiment, L is substituted or unsubstituted C2-C5 alkyl. In another embodiment, L is substituted or unsubstituted C2-C8 alkyl. In another embodiment, L is unsubstituted C2-C3 alkyl. In another embodiment, L is substituted C2-C3 alkyl.

In some embodiments, L of the poly-phosphonate of this invention is alkyl, aryl, alkylaryl, alkynyl, alkyl ether, alkyl thioether, alkyl amide, alkyl amine, or an amino side chain, wherein the alkyl, aryl, alkylaryl, alkynyl, alkyl ether, alkyl thioether, alkyl amide or alkyl amine is substituted or unsubstituted. The substituents are selected from halo, CN, $NO_2$, alkyl, OH, COOH, amine, hydroxy, alkoxy, aryloxy, alkylaryloxy, heteroaryloxy, oxo, cycloalkyl, phenyl, heteroaryls, heterocyclyl, naphthyl, amino, alkylamino, arylamino, heteroarylamino, dialkylamino, diarylamino, alkylarylamino, alkylheteroarylamino, arylheteroarylamino, acyl, acyloxy, carboxy, carbamoyl, carboxamide, cyano, sulfonyl, sulfonylamino, sulfinyl, sulfinylamino, thiol, alkylthio, arylthio, or alkylsulfonyl groups. Any substituents can be unsubstituted or further substituted with any one of these aforementioned substituents.

In some embodiments, the poly-phosphonate of this invention is encapsulated.

In another embodiments, the tetra-phosphonate compound is represented by the following structure (succinyl tetra phosphonate-SUTP) or alkali salt thereof:

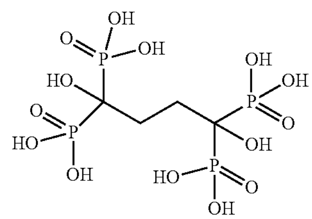 [SMILES: O=P(O)(O)C(O)(CCC(O)(P(=O)(O)O)P(=O)(O)O)P(=O)(O)O]

In another embodiments, the tetra-phosphonate compound is represented by the following structure (malonyl tetra phosphonate) or alkali salt thereof:

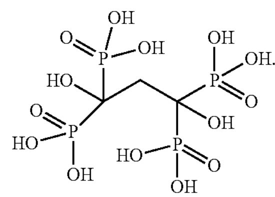

In some embodiments, provided herein a dental care composition comprising at least one poly-phosphonate in an amount of 0.05%-30% by weight of said composition; and a pharmaceutically acceptable carrier; wherein the poly-phosphonate comprises bisphosphonate compound or tetra-phosphonate compound; wherein the bisphosphonate is represented by the following structure or salt thereof:

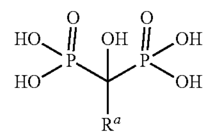

wherein $R^a$ is an amino acid, wherein the side chain of the amino acid is attached to the carbon; and wherein the tetra-phosphonate compound is represented by the following structures (succinyl tetra phosphonate (-SUTP) or alkali salt thereof; or a malonic tetra phosphonate or alkali salt thereof:

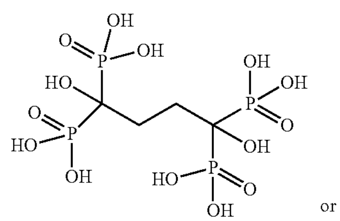

or

-continued

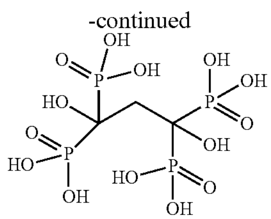

for use in removing tartar from the tooth surface of a subject. In another embodiment, the tartar is mature tartar.

In one embodiment, the hydroxy groups of the poly phosphate can be ionized depending in pH environment. In another embodiment, the ionization of the hydroxy groups of the poly phosphate include alkali salt thereof.

In another embodiment, the alkali salt of the tetra-phosphonate compound, bisphosphonate compound, poly-phosphonate or the structure of formula I, is Li+, Na+, K+, Rb+, or Cs+. In another embodiment, the alkali salt is Na+.

In one embodiment, this invention provides a succinyl tetra phosphonate compound represented by the following structure or alkali salt thereof:

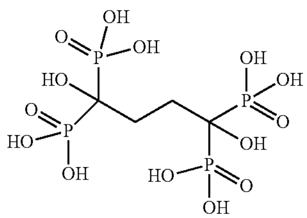 [SMILES: O=P(O)(O)C(O)(CCC(O)(P(=O)(O)O)P(=O)(O)O)P(=O)(O)O]

In one embodiment, this invention provides a composition comprising a succinyl tetra phosphonate compound represented by the following structure or alkali salt thereof:

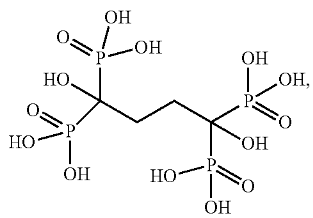 [SMILES: O=P(O)(O)C(O)(CCC(O)(P(=O)(O)O)P(=O)(O)O)P(=O)(O)O]

and a pharmaceutically acceptable carrier. In another embodiment, the composition, is a dental care composition.

In one embodiment, this invention provides a composition comprising a succinyl tetra phosphonate compound represented by the following structure or alkali salt thereof:

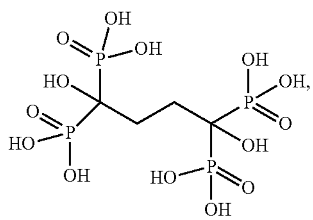 [SMILES: O=P(O)(O)C(O)(CCC(O)(P(=O)(O)O)P(=O)(O)O)P(=O)(O)O]

and a pharmaceutically acceptable carrier, for use as a calculus removal agent. In another embodiment, the composition is for use as mature calculus removal agent.

In one embodiment, this invention provides a dental care composition comprising a succinyl tetra phosphonate compound for use in treating teeth for removing mature tartar from the tooth surface of a subject.

In one embodiment, this invention provides a malonic tetra phosphonate compound represented by the following structure or alkali salt thereof:

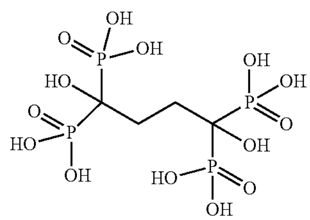 [SMILES: O=P(O)(O)C(O)(CCC(O)(P(=O)(O)O)P(=O)(O)O)P(=O)(O)O]

In one embodiment, this invention provides a composition comprising a malonic tetra phosphonate compound represented by the following structure or alkali salt thereof:

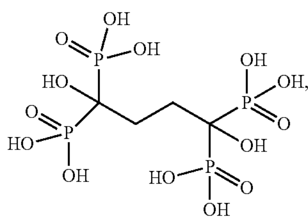 [SMILES: O=P(O)(O)C(O)(CCC(O)(P(=O)(O)O)P(=O)(O)O)P(=O)(O)O]

and a pharmaceutically acceptable carrier. In another embodiment, the composition, is a dental care composition.

In one embodiment, this invention provides a composition comprising a succinyl tetra phosphonate compound represented by the following structure or alkali salt thereof:

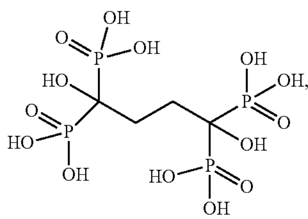 [SMILES: O=P(O)(O)C(O)(CCC(O)(P(=O)(O)O)P(=O)(O)O)P(=O)(O)O]

and a pharmaceutically acceptable carrier, for use as an calculus removal agent, as an anti dental caries, or combination thereof.

In one embodiment, this invention provides a dental care composition comprising a malonic tetra phosphonate compound for use in treating teeth for removing tartar from the tooth surface of a subject. In another embodiment, the tartar is mature tartar.

N-Halamine

The term "N-halamine" refers herein to N-halamine compound, N-halamine based polymer and/or N-halamine particle if not referred specifically to the N-halamine compound, N-halamine based polymer and/or N-halamine particle.

In another embodiment, "N-halamine", refers to N-halamine compound. In another embodiment, "N-halamine", refers to N-halamine based polymer. In another embodiment, "N-halamine", refers to N-halamine based particle.

In another embodiment, the N-halamine compound comprises a halogenated primary amine, a halogenated secondary amine, a halogenated amide or a halogenated urea.

In another embodiment, the N-halamine based particle is a nanoparticle or a microparticle.

In another embodiment, the N-halamine based polymer is a nanoparticle or a microparticle.

In another embodiment, the N-halamine compound, N-halamine based polymer, or N-halamine based particle is encapsulated.

In some embodiments, the dental care composition of this invention comprises a N-halamine compound. In other embodiments, the N-halamine compound comprises a halogenated primary amine, secondary amine, a tertiary amine, a primary or secondary amide, an imine, or an urea. In other embodiments, the N-halamine is N-chloroamine. In other embodiments, the N-halamine is N-bromoamine. In other embodiments, the N-halamine is N-iodoamine. In other embodiments, the N-halamine is N-fluoroamine.

Examples of N-halamine compounds include N-chloroglycine, N-Bromoglycine, N-iodoglycine, N-chlorosarcosine, N-bromosarcosine, N-iodosarcosine, N-chloro alpha amino isobutyric acid, N-chlorotaurine, N-bromotaurine, N-iodotaurine, N-chloroaminomethanesulfonic acid N-chloroethanolamine, N-chloro-N-acetyl glycine, N-bromoethanolamine, N-iodoethanolamine, N-iodo-N-acetyl glycine, N-bromo N-acetyl glycine, N-chloroalanine, N-chloro beta alanine, N-bromo beta alanine, N-chloroserine, N-bromoserine, N-iodoserine, N-chloro-N-phenylalanine, N-chloroisoleucine, N-chloro-norvaline, N-chloroleucine, N-bromoleucine, N-iodoleucine, N-chloroproline, N-bromoproline, N-iodoproline, N-chloro hydroxyproline, N-chloro omega aminoundecanoic acid, N-chloroaspartic acid, N-bromoaspartic acid, N-chloroglutamic acid, N-iodoglutamic acid, N-chlorovaline, N-chlorotyro sine, N-bromo-tyro sine, N-iodotyrosine, N-chloroethreonine, N-chlorocysteine, N-chlorocystine, N-chloromethionine, N-chlorohistidine, N-chloroarginine, N-chloroglutamine, N-bromoglutamine, N-chlorolysine, N-chloro gamma aminobutyric acid, N-chloro alpha, epsilon diaminopimelic acid, N-chloroornithine, N-chloro hydroxy lysine, N-chloroanthranilic acid, N-chloro p-aminobenzoic acid, N-chlorosulfanilic acid, N-chloro phenylsulfamic acid, N-chloro aminopropanesulfonic acid, N-chloro-propanolamine, N-chloro-diethanolamine, N-chloro ethylene diamine tetraacetic acid.

In some embodiments, the dental care composition of this invention comprises a N-halamine based polymer. In other embodiments, the N-halamine polymer forms a nanoparticle or a microparticle.

In another embodiment, the N-halamine based particle is in a form of a core/shell silica halamine-urea particles represented by the following structure:

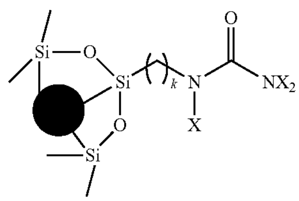

wherein X is independently a halide and k is an integer between 1-10. In another embodiment, the halide is chloride.

In another embodiment, the N-halamine polymer is represented by the following structures:

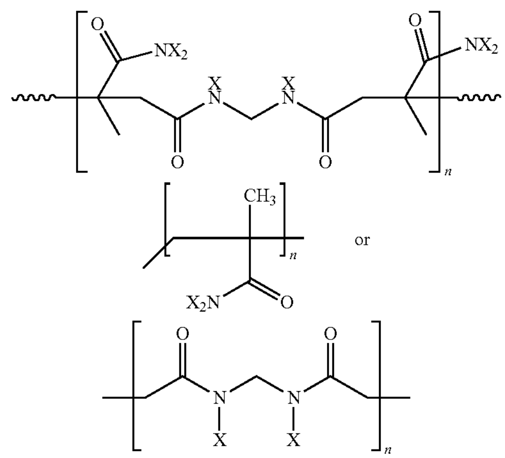

wherein

X is independently a halide and n is between 2-100. In another embodiment, the halide is chloride.

In some embodiment, k of N-halamine based particle is an integer between 1-10. In another embodiment, k is an integer between 1-5. In another embodiment, k is an integer between 2-5. In another embodiment, k is an integer between 1-8. In another embodiment, k is an integer between 2-8. In another embodiment, k is an integer between 3-5. In another embodiment, k is an integer between 2-10. In another embodiment, k is 1. In another embodiment, k is 2. In another embodiment, k is 3. In another embodiment, k is 4. In another embodiment, k is 5. In another embodiment, k is 6. In another embodiment, k is 7. In another embodiment, k is 8. In another embodiment, k is 9. In another embodiment, k is 10.

In some embodiments, n of N-halamine based polymer is an integer between 2-100. In another embodiment, n is between an integer 10-20. In another embodiment, n is between 20-30. In another embodiment, n is between an integer 30-40. In another embodiment, n is between 40-50. In another embodiment, n is an integer between 50-60. In another embodiment, n is an integer between 60-70. In another embodiment, n is between 70-80. In another embodiment, n is an integer between 80-90. In another embodiment, n is an integer between 90-100. In another embodiment, n is an integer between 2-20. In another embodiment, n is an integer between 2-30. In another embodiment, n is an integer between 2-40. In another embodiment, n is an integer between 2-50. In another embodiment, n is an integer between 2-60. In another embodiment, n is an integer between 2-70. In another embodiment, n is an integer between 2-80. In another embodiment, n is an integer between 2-90. In another embodiment, n is an integer between 2-80. In another embodiment, n is an integer between 5-25. In another embodiment, n is an integer between 2-80. In another embodiment, n is an integer between 25-50. In another embodiment, n is an integer between 2-80. In another embodiment, n is an integer between 50-75. In another embodiment, n is an integer between 2-80. In another embodiment, n is an integer between 75-100.

In some embodiments, the dental care composition, comprises a N-halamine based polymer, (the halogenation is both on the primary and secondary amides) is represented by the following structure:

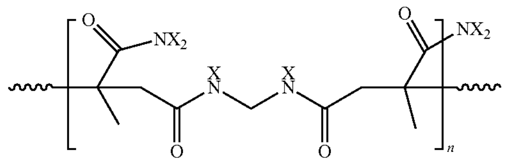

wherein X is independently a halide and n is between 2-100. In another embodiment, X is Cl.

In some embodiments, the dental care composition, comprises a polymerized N-halamine, and is represented by the following structure:

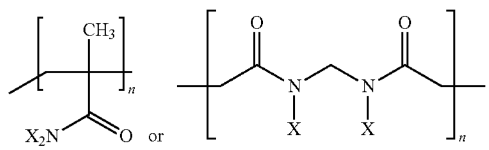

wherein X is independently a halide and n is an integer between 2-100. In another embodiment, X is Cl.

In some embodiment, provided herein, a dental care composition comprising N-halamine compound, N-halamine based polymer, or N-halamine based particle is in an amount of 0.1%-10% by weight of said composition; and a pharmaceutically acceptable carrier for use in removing of tartar from the tooth surface of a subject. In another embodiment, the tartar is mature tartar.

In another embodiment, the N-halamine compound comprises a halogenated primary amine, a halogenated secondary amine, a halogenated amide or a halogenated urea.

In some embodiments, provided herein, a dental care composition comprising of N-halamine based polymer or N-halamine based particle in an amount of 0.1-10% by weight of said composition, and a pharmaceutically acceptable carrier, wherein the N-halamine based polymerized is represented by the following structures:

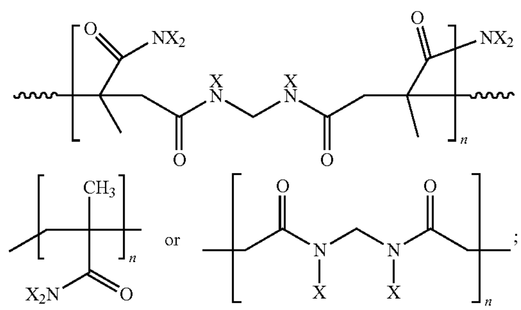

N-halamine based particle is in a form of a core/shell silica halamine-urea particles represented by the following structure:

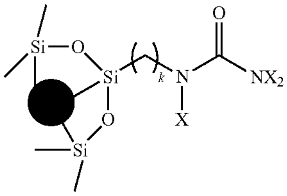

wherein X is a halide and k is between 1-10, for use in treating or preventing dental caries and/or for treating or preventing periimplantitis or periodontal diseases.

As used herein, the term "alkyl", refers, in one embodiment, to a "$C_1$ to $C_{12}$ alkyl" and denotes linear and branched, saturated or unsaturated (e.g., alkenyl, alkynyl) groups, the latter only when the number of carbon atoms in the alkyl chain is greater than or equal to two, and can contain mixed structures. Non-limiting examples are alkyl groups containing from 1 to 6 carbon atoms ($C_1$ to $C_6$ alkyls), or alkyl groups containing from 1 to 4 carbon atoms ($C_1$ to $C_4$ alkyls). Examples of saturated alkyl groups include, but are not limited to, methyl, ethyl, n-propyl, isopropyl, n-butyl, iso-butyl, sec-butyl, tert-butyl, amyl, tert-amyl and hexyl. Examples of alkenyl groups include, but are not limited to, vinyl, allyl, butenyl and the like. Examples of alkynyl groups include, but are not limited to, ethynyl, propynyl and the like. Similarly, the term "$C_1$ to $C_{12}$ alkylene" denotes a bivalent radical of 1 to 12 carbons.

The alkyl group can be unsubstituted, or substituted with one or more substituents selected from the group consisting of halogen, hydroxy, alkoxy, aryloxy, alkylaryloxy, heteroaryloxy, oxo, cycloalkyl, phenyl, heteroaryls, heterocyclyl, naphthyl, amino, alkylamino, arylamino, heteroarylamino, dialkylamino, diarylamino, alkylarylamino, alkylheteroarylamino, arylheteroarylamino, acyl, acyloxy, nitro, carboxy, carbamoyl, carboxamide, cyano, sulfonyl, sulfonylamino, sulfinyl, sulfinylamino, thiol, alkylthio, arylthio, or alkylsulfonyl groups. Any substituents can be unsubstituted or further substituted with any one of these aforementioned substituents.

The term "aryl" used herein alone or as part of another group denotes an aromatic ring system containing from 6-14 ring carbon atoms. The aryl ring can be a monocyclic, bicyclic, tricyclic and the like. Non-limiting examples of aryl groups are phenyl, naphthyl including 1-naphthyl and 2-naphthyl, and the like. The aryl group can be unsubstituted or substituted through available carbon atoms with one or more groups such as halogen, hydroxy, alkoxy, aryloxy, alkylaryloxy, heteroaryloxy, oxo, cycloalkyl, phenyl, heteroaryls, heterocyclyl, naphthyl, amino, alkylamino, arylamino, heteroarylamino, dialkylamino, diarylamino, alkylarylamino, alkylheteroarylamino, arylheteroarylamino, acyl, acyloxy, nitro, carboxy, carbamoyl, carboxamide, cyano, sulfonyl, sulfonylamino, sulfinyl, sulfinylamino, thiol, alkylthio, arylthio, or alkylsulfonyl groups. Any substituents can be unsubstituted or further substituted with any one of these aforementioned substituents.

The term "salt" refers to any known inorganic or organic salt. The term "salt" of a given compound refers to salts that retain the biological effectiveness and properties of the given compound, and which are not biologically or otherwise undesirable. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, methanesulfonic acid, ethanesulfonic acid, p-toluene-sulfonic acid, and the like. In another embodiment, the term "salt" refers to pharmaceutically acceptable organic or inorganic base or residue of a base, selected from the group consisting of alkali metals, alkaline earth metals, aluminum, zinc and ammonium. The pharmaceutically acceptable base addition salts may be prepared from inorganic and organic base. Salts derived from inorganic base include NaOH, KOH, and the like. Salts derived from organic base include $NH_4OH$, $NH_3$, and the like.

In another embodiment, the pharmaceutically acceptable salt includes inorganic cation selected from the group consisting of lithium, sodium, potassium, calcium, magnesium, aluminum, zinc and ammonium. Each possibility represents a separate embodiment of the present invention.

In another embodiment, the salt is an alkali salt.

The term "alkali salt" refers to alkali cation. The alkali salt of the polyphosphonate provided herein, refers to at least one of the OH groups on the phosphonate group being O-M+, wherein M+ is an alkali cation.

An "alkali cation" refers herein to $Li^+$, $Na^+$, $K^+$, $Rb^+$, or $Cs^+$.

In some embodiments, the dental care composition of this invention comprises a polymerized phosphonate. In other embodiments, the polymerized phosphonate forms a nanoparticle or a microparticle. It well-known that nanoparticles have a high surface area and therefore the effect of the active groups on their surface may increase.

A "halide" refers herein to Cl, F, Br or I. In one embodiment, the halide is chloride. In other embodiment, the halide is fluoride. In other embodiment, the halide is bromide. In other embodiments, the halide is iodide.

In some embodiment, the dental care composition of this invention comprises a co-polymer, wherein the co-polymer comprises a poly-phosphonate backbone and a poly-N-halamine backbone. In other embodiments the poly-phosphonate backbone comprises poly-bisphosphonate backbone. In other embodiment non limiting examples of poly-phosphonate backbone comprises Poly(styryl bisphosphonate) or polyethyleneglycol bisphosphonate. In other embodiments, the co-polymer is in a form of nanoparticle or a microparticle.

The term "backbone" refers to the monomeric unit comprising each a N-halamine or a phosphonate group of the co-polymer.

In some embodiments this invention provides a dental care composition comprising at least one poly-phosphonate, N-halamine or combination thereof; or a co-polymer comprising a poly-phosphonate backbone and a poly-N-halamine backbone; and a pharmaceutically acceptable carrier, wherein the poly-phosphonate, the N-halamine and/or the co-polymer is encapsulated. In another embodiment, the poly-phosphonate is encapsulated. In another embodiment, the N-halamine is encapsulated. In another embodiment, the co-polymer is encapsulated. In another embodiment, provided herein is a composition encapsulated in a form of a core shell silica urea particles Non limiting examples for encapsulating the calculus removal agent of this invention can be found in U.S. Pat. No. 10,508,126.

The term "removing mature tartar" of this invention refers to removal or decompose of octacalcium phosphate $Ca_4H(PO_4)_3 \cdot 2H_2O$, hydroxapetite $Ca_{10}(OH)_2(PO4)_6$ and/or whitlockite $Ca_9(PO_4)_6XPO_4$ from the tooth surface of a subject.

In some embodiments, the term "remove" refer to complete removal of the tartar or mature tartar from the tooth surface of a subject.

In another embodiment, the removal of the tartar to mature tartar refer to at least 50% from the tooth surface. In another embodiment, the removal of the tartar to mature tartar refer to at least 60% from the tooth surface. In another embodiment, the removal of the tartar to mature tartar refer to at least 70% from the tooth surface. In another embodiment, the removal of the tartar to mature tartar refer to at least 75% from the tooth surface. In another embodiment, the removal of the tartar to mature tartar refer to at least 80% from the tooth surface. In another embodiment, the removal of the tartar to mature tartar refer to at least 85% from the tooth surface. In another embodiment, the removal of the tartar to mature tartar refer to at least 90% from the tooth surface. In another embodiment, the removal of the tartar to mature tartar refer to at least 95% from the tooth surface.

In some embodiment, the complete removal of the tartar or mature tartar is after repeated administration or application of the composition of this invention.

In some embodiment, the complete removal of the tartar or mature tartar is after repeated administration or application of the composition of this invention, followed by brushing the teeth.

A pharmaceutical acceptable carrier for the dental care composition of this invention refers to a suitable carrier a suitable vehicle that can be used to apply the present composition to the oral mucosa.

Suitably, in compositions of the present invention, the orally acceptable vehicle may comprise other components such as, flavorings, coloring agents, sweeteners, humectants, thickening agents, binders and surfactants.

Binders and thickening agents can be added to assure physical integrity in pastes, gels, films and liquid pastes. Preferred thickening and binding agents include for example natural and synthetic gums such as xanthan and acacia gums, carageenans, alginates, cellulose ethers and esters such as carboxy methyl cellulose, polyoxyalkyl polymers such as the Pluronics polymers, PVP materials, certain polymers exemplified by the carboxyvinyl polymers, and silica.

In addition, the orally acceptable vehicle may optionally comprise surfactants, sweetening agents, flavoring agents, anticaries agents (in addition to a fluoride ion source provided as a phosphatase enzyme inhibitor), anti-plaque agents, anti-bacterial agents such as cetyl pyridinium chloride, tooth desensitizing agents, coloring agents and pigments.

The composition of this invention can be formulated as a mouthwash or mouth rinse as well. A mouth wash or rinse will contain up to 95% water, up to 30% alcohol, flavor, polyhydric alcohols, anti-caries agents, plaque removing agents, sweeteners, dyes and lakes.

The active materials could also be incorporated into currently existing formulations including non-limiting examples such as Cepacol (Lakeside Pharmaceuticals), Plax, (Pfizer), Scope (Procter & Gamble), and the like In some embodiments, the composition of this invention is a solution. In another embodiment, the solution is at pH of between 3.0-9.5. In another embodiment, the solution is acidic. In another embodiment, the solution is basic.

Methods

This invention provides a method for (i) removing tartar from the tooth surface of a subject; (ii) removing mature tartar (mature calculus) from the tooth surface of a subject; (iii) treating or preventing dental caries; (iv) treating or preventing periimplantitis; (v) treating or preventing periodontal; by administering a composition provided herein. Each represent a separate embodiment of this invention.

This invention provides a method for removing tartar from the tooth surface by administering/applying a composition of this invention to the tooth surface in need.

This invention provides a method for removing mature tartar (mature calculus) from the tooth surface of a subject by administering/applying a composition of this invention to the tooth surface in need.

This invention provides a method for removing mature tartar (mature calculus) from the tooth surface of a subject by repeated administration or application of the composition of this invention to the tooth surface in need.

This invention provides a method for treating or preventing dental caries by administering/applying a composition of this invention to the tooth surface in need.

This invention provides a method for treating or preventing periimplantitis by administering/applying a composition of this invention to the tooth surface in need.

This invention provides a method for treating or preventing periodontal by administering/applying a composition of this invention to the tooth surface in need.

In other aspects, this invention provides a method of treating teeth for (i) removing tartar from the tooth surface of a subject; (ii) removing mature tartar (mature calculus) from the tooth surface of a subject; (iii) treating or preventing dental caries; (iv) treating or preventing periimplantitis; or (v) treating or preventing periodontal; applying a composition of this invention to the tooth in need whilst leaving the remainder of the tooth unaffected. (e.g. the dentine or enamel, entirely unaffected). Each represents a separate embodiment of this invention.

In other aspects, this invention provides a method of treating teeth for removing or reducing tartar from the tooth surface of a subject and therefore preventing the building up of plaque and/or tartar by applying a composition of this invention to the tooth in need, whilst leaving the remainder of the tooth unaffected. (e.g. the dentine or enamel, entirely unaffected). Each represents a separate embodiment of this invention.

In other aspects, this invention provides a method of treating teeth for (i) removing tartar from the tooth surface of a subject; (ii) removing mature tartar (mature calculus) from the tooth surface of a subject; or (iii) treating or preventing dental caries by applying a composition of this invention to the tooth in need thus reducing the needs of mechanical removal by drills, burrs and hand tools to a minimum of eliminating them completely. Each represents a separate embodiment of this invention.

In other aspects, this invention provides a method of treating teeth for removing tartar from the tooth surface of a subject and therefore preventing the building up of plaque and/or tartar by applying a composition of this invention to the tooth in need, thus reducing the needs of mechanical removal by drills, burrs and hand tools to a minimum of eliminating them completely. In another embodiment, the tartar is mature tartar.

This invention provides a method for (i) removing tartar from the tooth surface of a subject; (ii) removing mature tartar (mature calculus) from the tooth surface of a subject; (iii) preventing building up of tartar formation on a tooth surface of a subject; (iv) treating or preventing dental caries; (v) treating or preventing periimplantitis; or (vi) treating or preventing periodontal; by administering a composition comprising poly-phosphonate or salt thereof provided herein to the tooth in need.

This invention provides a method for (i) removing tartar from the tooth surface of a subject; (ii) removing mature tartar (mature calculus) from the tooth surface of a subject; (iii) preventing building up of tartar formation on a tooth surface of a subject; (iv) treating or preventing dental caries; (v) treating or preventing periimplantitis; or (vi) treating or preventing periodontal; by administering a composition comprising N-halamine provided herein to the tooth in need.

This invention provides a method for (i) removing tartar from the tooth surface of a subject; (ii) removing mature tartar (mature calculus) from the tooth surface of a subject; (iii) preventing building up of tartar formation on a tooth surface of a subject; (iv) treating or preventing dental caries; (v) treating or preventing periimplantitis; or (vi) treating or preventing periodontal; by administering a combination of N-halamine and poly phosphonate wherein the N-halamine and polyphosphonates are administered sequentially or concomitantly in either order. Each represents a separate embodiment of this invention.

This invention provides a method for (i) removing tartar from the tooth surface of a subject; (ii) removing mature tartar (mature calculus) from the tooth surface of a subject; (iiii) treating or preventing dental caries; (iv) treating or preventing periimplantitis; or (v) treating or preventing periodontal; by administering a combination of N-halamine and co-polymer comprising a phosphonate backbone and a N-halamine backbone; wherein the N-halamine and co-polymer are administered sequentially or concomitantly in either order. Each represents a separate embodiment of this invention.

This invention provides a method for (i) removing tartar from the tooth surface of a subject; (ii) removing mature tartar (mature calculus) from the tooth surface of a subject; (iii) treating or preventing dental caries; (iv) treating or preventing periimplantitis; or (v) treating or preventing periodontal; by administering a combination of poly-phosphante and co-polymer comprising a phosphonate backbone and a N-halamine backbone; wherein the poly-phosphante and co-polymer are administered sequentially or concomitantly in either order. Each represents a separate embodiment of this invention.

Regimen

In some embodiments, this invention provides a regimen for removing tartar, from the teeth of a subject, wherein the regimen comprises applying the dental care composition of this invention to the tooth. In some embodiments, this invention provides a regimen for removing tartar, from the teeth of a subject, wherein the regimen comprises applying the dental care composition of this invention to the tooth, followed by brushing the teeth. In some embodiments, this invention provides a regimen for removing tartar, from the teeth of a subject, wherein the regimen comprises repeated application of the dental care composition of this invention to the tooth. In some embodiments, this invention provides a regimen for removing tartar, from the teeth of a subject, wherein the regimen comprises repeated application of the dental care composition of this invention to the tooth, followed by brushing the teeth.

This invention provides a regimen for (i) removing tartar from the tooth surface of a subject; (ii) removing mature tartar (mature calculus) from the tooth surface of a subject; (iii) treating or preventing dental caries; (iv) treating or preventing periimplantitis; or (v) treating or preventing periodontal; wherein the regimen comprises applying the dental care composition of this invention to the teeth, and optionally followed by brushing the teeth.

This invention provides a regimen for (i) removing tartar from the tooth surface of a subject; (ii) removing mature tartar (mature calculus) from the tooth surface of a subject; (iii) treating or preventing dental caries; (iv) treating or preventing periimplantitis; or (v) treating or preventing periodontal; wherein the regimen comprises applying the dental care composition of this invention on a dental implant.

In one embodiment, a regimen (i) removing tartar from the tooth surface of a subject; (ii) removing mature tartar (mature calculus) from the tooth surface of a subject; (iii) treating or preventing dental caries; (iv) treating or preventing periimplantitis; or (v) treating or preventing periodontal; comprises applying the dental care composition provided to the tooth for 2 minutes, 5 minutes, 10 minutes, 20 minutes, 30 minutes, 40 minutes, 50 minutes or for 1 hour. In another embodiment, a regimen for (i) removing or reducing tartar from the tooth surface of a subject; (ii) removing or reducing mature tartar (mature calculus) from the tooth surface of a subject; (iii) treating or preventing dental caries; (iv) treating or preventing periimplantitis; or (v) treating or preventing periodontal; comprises applying the dental care composition of this invention to the teeth once a day, twice a day, once a week, twice weekly and optionally followed by brushing the teeth.

In another embodiment, a regimen for (i) removing or reducing tartar from the tooth surface of a subject; (ii) removing or reducing mature tartar (mature calculus) from the tooth surface of a subject; (iii) treating or preventing dental caries; (iv) treating or preventing periimplantitis; or (v) treating or preventing periodontal; comprises applying the dental care composition of this invention to the teeth once a day, twice a day, once a week, twice weekly; wherein the composition is applied by swashing with mouth wash or applying a toothpaste or applying a dental tray.

The following non-limiting examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1

Synthesis of Succinyl Tetra Phosphonate (SUTP, Scheme 1)

Scheme 1

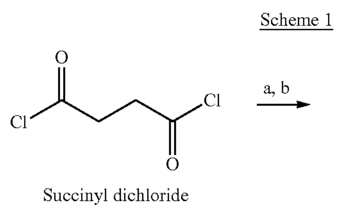

Succinyl dichloride

-continued

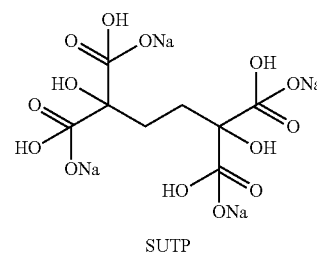

SUTP

Synthesis of SUTP: a) $P(OSiMe_3)_3$, THF, 0° C. to R.T. b) MeOH, NaOH, R.T.

Succinyl dichloride (3.5 ml, 5 g, 0.03 mol) was dissolved in THF (100 ml) in a nitrogen environment and placed in an ice bath. Tris(trimethylsilyl) phosphite (46.8 ml, 41.8 g, 0.14 mol) was added and the resulting yellow mixture was then allowed to reach RT and then was stirred for 24 h. Then, the mixture was evaporated to dryness, then methanol (200 ml) was added, yielding an orange solution which was then was stirred for 24 h at RT resulting in a white precipitate. The white solid was collected by Buckner filtration and washed with methanol (100 ml), yielding a yellow filtrate. This was dried by vacuum to give the desired compound, Succinyl tetra phosphonate (SUTP, FIGS. 1A-1D).

Example 2

Synthesis of γ-Glu-BP (Scheme 2)

Scheme 2

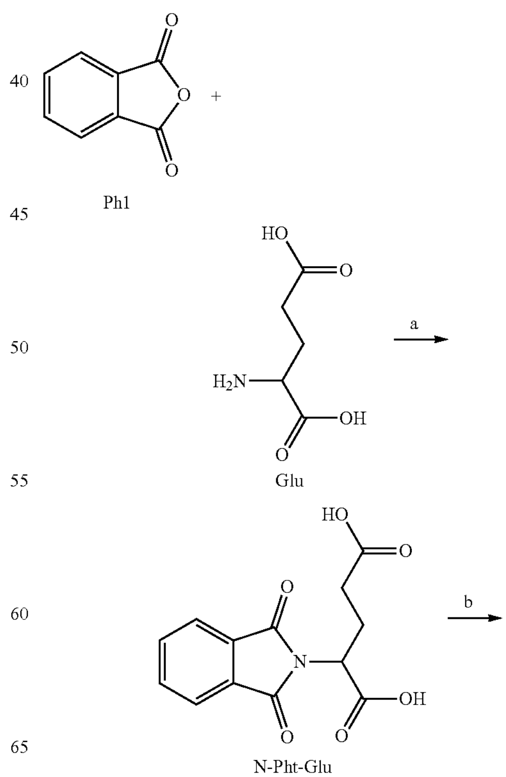

Ph1

Glu

N-Pht-Glu

-continued

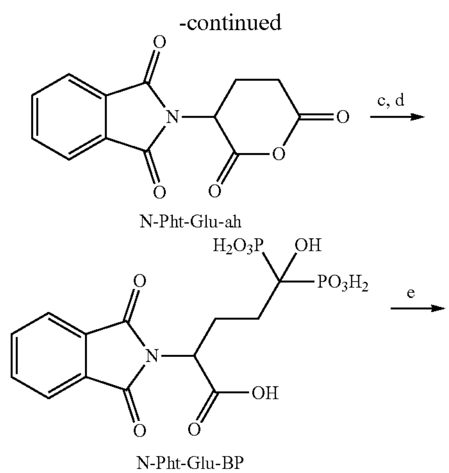

N-Pht-Glu-ah

N-Pht-Glu-BP

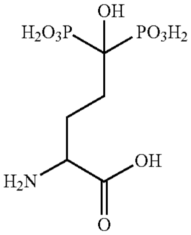

γ-Glu-BP

Synthesis of γ-Glu-BP: a) AcOH, 145° C., 1.5 h, 44.4%. b) $Ac_2O$, 100° C., 2 h. 91.6%. c) $P(OSiMe_3)$, THF, R.T., o.n. d) MeOH, R.T. 2 h, 83.3% (for two steps). E) HCl 6M, refluxed, o.n., 98.7%.

Synthesis of γ-N-Phthaloyl Glutamic Acid-step a

N-phthaloyl glutamic acid was synthesized as follows (Scheme 2-step a): Acetic acid (34 ml) was added to a 500 ml round bottom flask containing phthalic anhydride (12.88 g, 0.087 mol) and L-glutamic acid (17 g, 0.11 mol), resulting in a turbid solution. The solution was heated at 145° C. for 1.5 h giving a clear colorless solution. The solution was allowed to cool to room temperature, and then evaporated to give a colorless oil. Double distilled water (DDW) (334 ml) was then added to the oil and heated to 100° C., resulting in a clear colorless solution. The solution was then allowed to cool to room temperature, 32% HCl (6 ml) was added and the mixture was refrigerated overnight. The obtained solid was filtered and dried to yield the desired product (10.7 g. 44.4% yield).

Synthesis of N-Phthaloyl Glutamic Anhydride-step b

N-phthaloyl glutamic anhydride was synthesized as follows: A suspension of N-phthaloyl glutamic acid (10 g, 0.036 mol) in acetic anhydride (40 ml) was heated at 100° C. for 2 h to give a clear colourless solution, then cooled to room temperature and evaporated, yielding the desired compound, a white-pinkish solid (8.6 g, 91.6% yield).

Synthesis of N-Pht-Glu-BP-step c,d

N-phthaloyl glutamic anhydride (8 g. 0.031 mol) was dissolved in 200 ml of dry tetrahydrofuran (THF) under a nitrogen atmosphere, yielding a clear off-white solution. Tris(trimethylsilyl)phosphite (20 g, 0.07 mol) was then added to the solution and stirred overnight. The obtained clear colorless solution was evaporated resulting in a clear pinkish oil, which was then dissolved in methanol (150 ml) and stirred for 2 h to give a clear colorless solution. The methanol solution was evaporated, and the resulting orange oil was washed with diethyl ether (700 ml) and dried to yield the desired compound (10.8 g, 83.3% yield).

Synthesis of γ-Glu-BP-step e

N-Pht-Glu-BP (10.8 g, 0.036 mol) was dissolved in HCl solution (6M, 190 ml), and the clear colorless solution was refluxed overnight. The solution was cooled to room temperature and then refrigerated for 4 h. The resulting white crystals of phthalic acid were filtered, and the clear colorless filtrate was evaporated to yield the desired compound (5.9 g, 98.7% yield).

Example 3

Synthesis of the Monomer Styryl Bisphosphonate (StBP, Scheme 3)

Scheme 3: Synthesis scheme of the StBP monomer

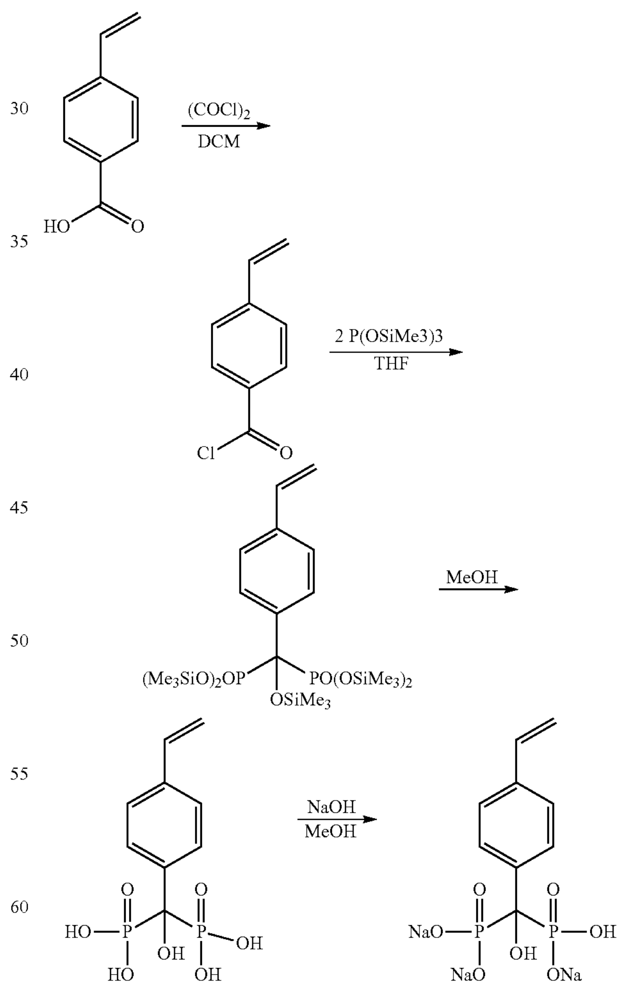

The StBP monomer was prepared as described as follows (Scheme 3): Oxalyl chloride (35 ml, 2 M) and N,N dimethylformamide (1 drop) were added to 4-vinylbenzoic acid (27 mmol) which was dissolved in anhydrous DCM (100 ml), and stirred overnight at room temperature (RT), producing 4-vinylbenzoyl chloride. The solution was evaporated producing a yellow oil, and then dissolved in anhydrous THF (100 ml). Tris(trimethylsilyl) phosphite (77 mmol) was added, and the mixture was stirred overnight at RT. The solution was evaporated yielding the desired compound. Anhydrous methanol (100 ml) was added followed by a 60 ml solution of NaOH (3.24 g) in methanol, and stirred for 2 h at RT. The product was filtered and washed of excess reagents with methanol and dried in vacuum (2 mmHg). The solid residue obtained (StBP monomer) was analyzed by nuclear magnetic resonance (NMR) spectroscopy, $^{1}H$, $^{13}C$ and $^{31}P$ NMR (Bruker DMX-600 spectrometer, 600.1, 150.9 and 242.9 MHz, respectively), Fourier transform infrared (FTIR-IR) analysis (Bruker ALPHA-FTIR, QuickSnap™, Germany), and elemental analysis (Perkin-Elmer 2400 series II Analyzer, Microanalysis Lab., Institute of Chemistry of The Hebrew University of Jerusalem, Jerusalem, Israel).

Example 4

Synthesis of the Cross-Linked Poly(Styryl Bisphosphonate) Nanoparticles (Poly(StBP) NPs, Scheme 4)

Scheme 4: Synthesis of poly(StBP) NPs.

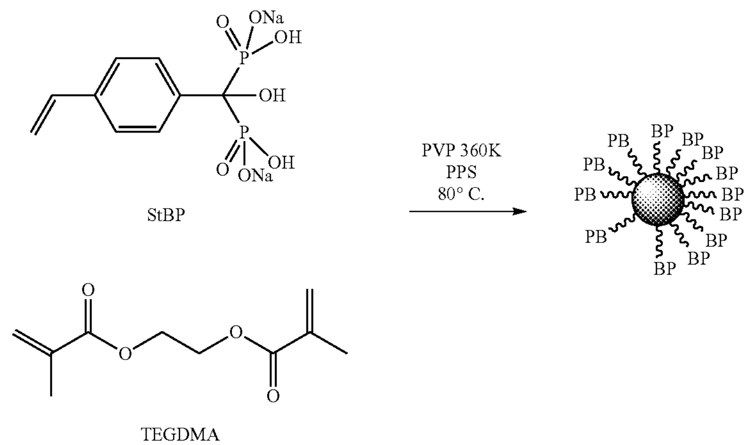

StBP

TEGDMA

Poly(StBP) NPs with a dry diameter of 65±7 nm (hydrodynamic diameter of 149±15 nm) were synthesized by a dispersion copolymerization process in 0.3 M HCl aqueous solution (2.5 ml) containing 1-propanol (40% (v/v)), with a total monomers concentration of 5% (w/v): 57.25 mg StBP monomer described in Example 3, and 62.5 mg TEGDMA [triethylene glycol dimethacrylate]. In addition, 6.25 mg of PPS (5% (w/w))[potassium persulphate] as initiator and 25 mg PVP [polyvinyl pyrrolidone] of 360K molecular weight (1% w/v) as stabilizer were added to the monomer solution.

Prior to the polymerization, the vial containing the mixture was purged with $N_2$ to exclude air and shaken at 80° C. overnight. The obtained particles were washed of excess reagents by extensive dialysis cycles (cut-off of 1,000 kD) with DDW. The particle dispersion was concentrated using hollow fiber diafiltration (750 kD polysulfone membrane, Spectrum Labs MiniKros® Sampler Plus P/N M4AB-260-01P).

Example 5

Chloramine Nano/Micro-Particles

Scheme 6: Synthesis of cross-linked P(MAA-MBAA) NPs

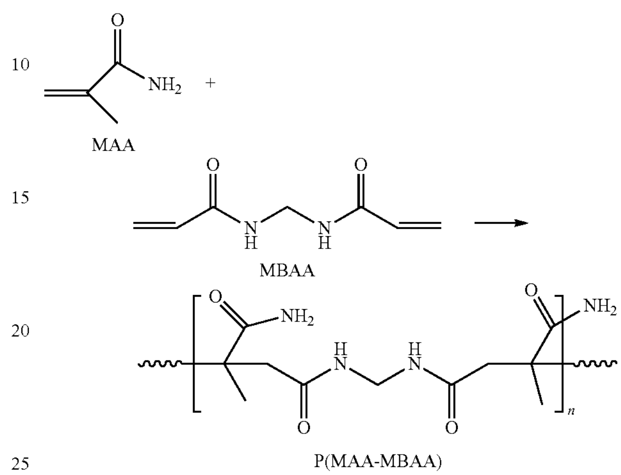

MAA

MBAA

P(MAA-MBAA)

Preparation of the Cross-Linked P(MAA–MBAA) Nanoparticles (Scheme 6)

Preparation of the cross-linked P(MAA–MBAA) nanoparticles (Scheme 6) P(MAA–MBAA) nanoparticles of hydrodynamic sizes ranging from 18±2 to 460±60 nm were formed by surfactant-free dispersion copolymerization of the monomers MAA and MBAA in water as a continuous phase. In brief, P(MAA–MBAA) nanoparticles of 27±3 nm hydrodynamic diameter were formed by dissolution of 4.4 g of MAA, 3.6 g of MBAA (2% w/v total monomers), and 240 mg of PPS in 400 mL of distilled water.

The 1 L round-bottom flask containing this solution was stirred with a mechanical stirrer (200 rpm) at 100° C. for 1 h. The MAA and MBAA residues were subsequently removed from the nanoparticle aqueous dispersion by extensive dialysis against water. The dried P(MAA–MBAA) nanoparticles were obtained by lyophilization.

The percent conversion (polymerization yield) of the monomers to P(MAA-MBAA) nanoparticles was calculated using the following expression:

$$\text{Polymerization yield (weigh \%)} = \frac{Wp(MAA-MBAA)}{W(MAA-MBAA)} \times 100$$

where $W_{P(MMA\text{-}MBAA)}$ is the weight of the obtained dried P(MAA-MBAA) nanoparticles and $W_{(MAA+MBAA)}$ is the initial weight of the monomers MA and MBAA. P(MAA-MBAA) nanoparticles of different sizes were formed by varying various polymerization parameters, e.g., monomer concentration, initiator type, and concentration.

Chlorination of the P(MAA-MBAA) nanoparticles (Scheme 7)

Scheme 7: Chlorination of the cross-linked P(MAA-MBAA) NPs.

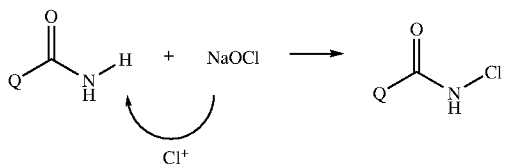

Sodium hypochlorite aqueous solution (5 mL, 4% w/v) was added to an aqueous dispersion of the P(MAA–MBAA) nanoparticles (5 mL, 15 mg/mL), which was shaken at room temperature for 1 h. Excess sodium hypochlorite was removed from the P(MAA–MBAA)-C1 nanoparticle dispersion by extensive dialysis against water.

The bound-C1 content of the P(MAA–MBAA)-C1 nanoparticles was determined by iodometric/thio sulfate titration according to the literature [32] using the following expression:

$$Cl^+(mM) = \frac{N \times V \times 1000}{2}$$

where N is the normality (equiv/L) and V is the volume (L) of the titrated sodium thio sulfate solution.

Other examples of polymerized halamine include NP/MP of halogenated poly MAA (methacrylamide) or halogenated poly MBAA (N, N methylene bisacrylamide):

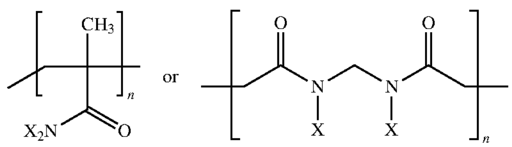

or wherein X is halide and n is an integer between 2 to 200.

Example 6

Preparation of Core and Core Shell Silica Halamine-Urea Particles (Scheme 8)

Preparation of Core and Core Shell Silica Urea Particles

Scheme 8: Synthesis of the $SiO_2$-urea N/MPs

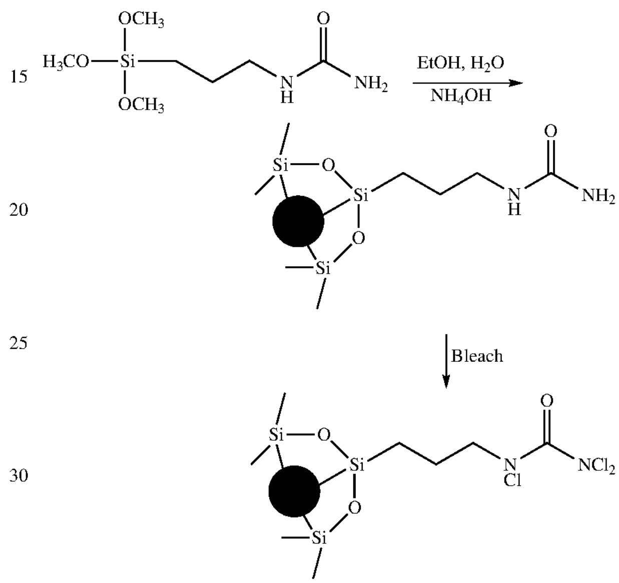

$SiO_2$-urea N/MPs were prepared using a modified Stöber polymerization process of tetraethylorthosilicate (TEOS) and 1-[3-(Trimethoxysilyl)propyl] urea (TMSPU). In a typical experiment, core particles were prepared by different amounts of ethanol absolute, deionized water, ammonium hydroxide, TEOS and TMSPU were added to a tube and shaken at room temperature for four hours. The formed $SiO_2$-urea N/MPs were then transferred to water by ethanol evaporation.

Core/shell $SiO_2$ urea NPs/MPs were prepared in two stages. First, the core $SiO_2$ NPs/MPs were prepared using a modified Stöer polymerization of tetraethylorthosilicate (TEOS). Thereafter, 1-[3-(Trimethoxysilyl)propyl] urea (TMSPU) was add to the tube and polymerized onto the previously produced $SiO_2$ N/MPs. The formed $SiO_2$-urea core/shell N/MPs were then transferred to water by ethanol evaporation. The chlorination of the core or core/shell SiO2-urea particles were accomplished with bleech as previously described.

Example 7

Effect of SUTP, poly(StBP) NPs, and γ-G1u-BP on Human Teeth

Figure 1C:
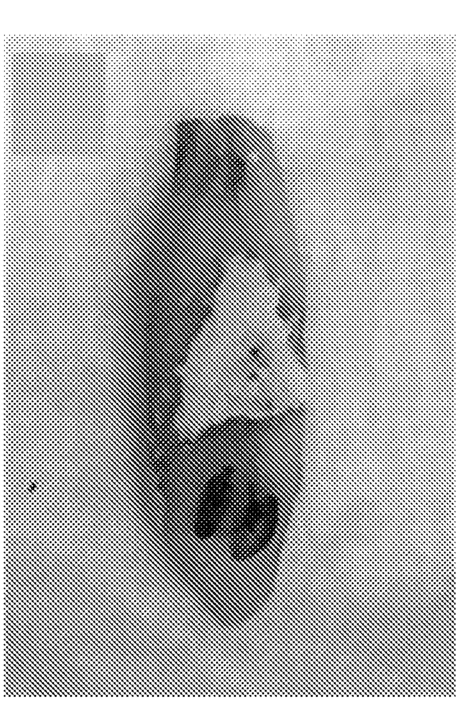
Figures 2A, 2B:
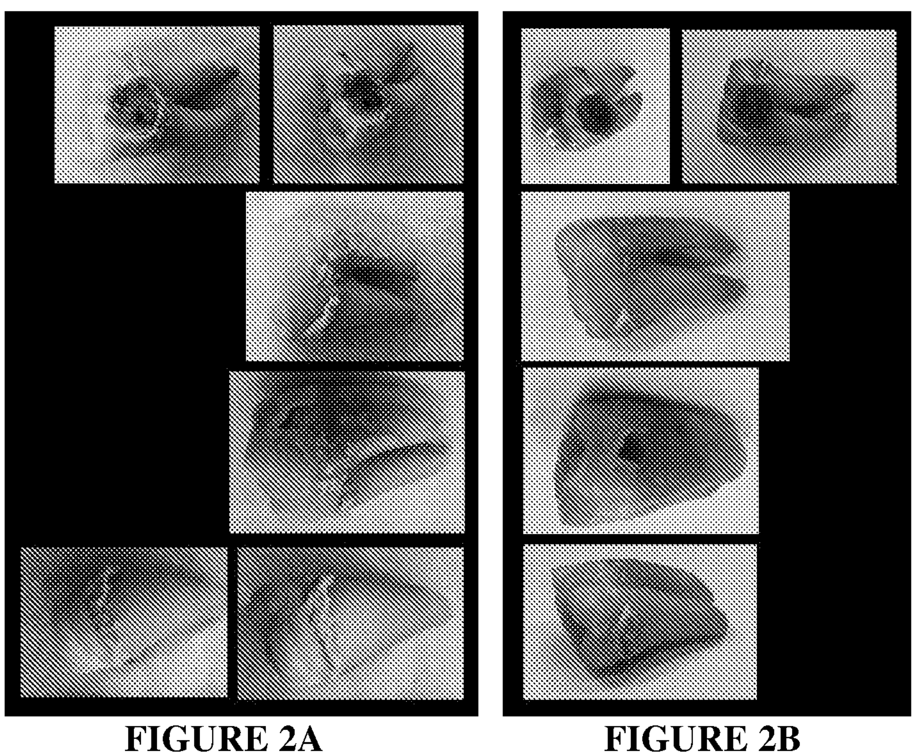
FIGS. 2A-2B presents pictures of human tooth with mature tartar before (FIG. 2A) and after (FIG. 2B) poly (styryl bisphosphonate) NPs (Poly(StBP) NPs) treatment (1 mg/ml)
Figures 3A, 3B:
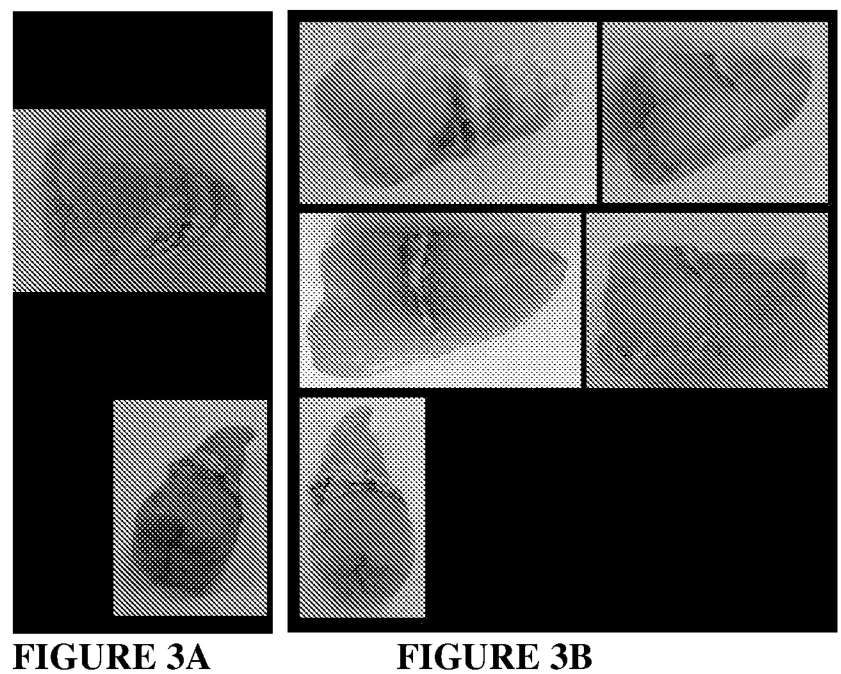
FIGS. 3A-3B presents pictures of human tooth with mature tartar before (FIG. 3A) and after (FIG. 3B) γ-Glu-BP treatment (1 mg/ml).

The effect of SUTP (Example 1), poly(StBP) NPs (Example 4), and γ-Glu-BP (Example 2) on human teeth was evaluated as followed:

Teeth were incubated in three separate aqueous solutions of: SUTP, poly(StBP) NPs, and γ-Glu-BP (1 mg/ml, 4 ml, pH=4) at RT for 1 hr. After 15 min of incubation, a new precipitate of tartar was observed spontaneously. The teeth were then brushed by a toothbrush to remove the remain tartar layer on the teeth and were incubated in new solutions of SUTP, poly(StBP) NPs, and γ-Glu-BP overnight. Then, the teeth were washed by DDW and were photographed. FIGS. 1-3 illustrate the cleaning of dirty teeth from tartar using SUTP (FIG. 1A-1D), poly(StBP) NPs (FIG. 2A-2B), and y-Glu-BP (FIG. 3A-3B) solutions.

Example 8

Effect of Halamine NPs on Human Teeth

The effect of halamines nanoparticles (as presented in Table 1) and SUTP compounds on mature tartar removal on human teeth were studied. 5 mL of each aqueous suspension were added to a 20 mL vial, and a tooth with tartar was added to each vial. Then, the solutions were stirred for 10 min at room temperature. After 10 minutes the teeth were brushed using a soft toothbrush and a photo of the tooth were taken.

TABLE 1

Suspensions content, concentration and pH used for studying the effect on tartar.

Figure 1B:
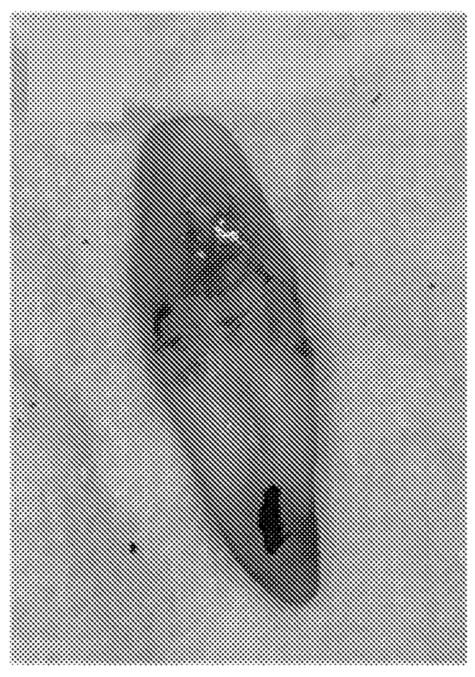
Figure 1D:
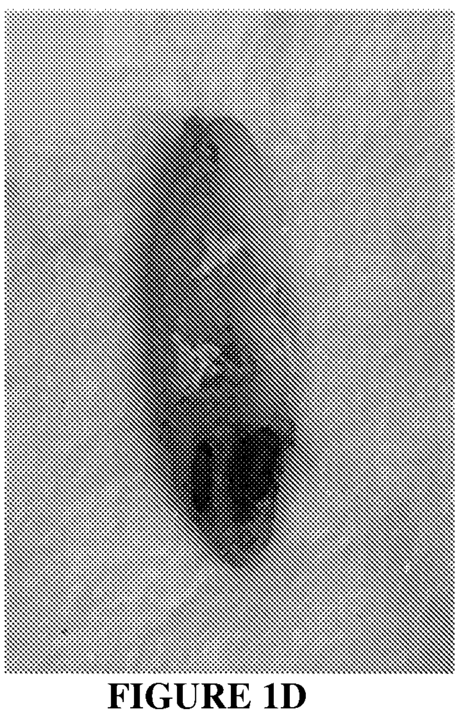
Figure 4A:
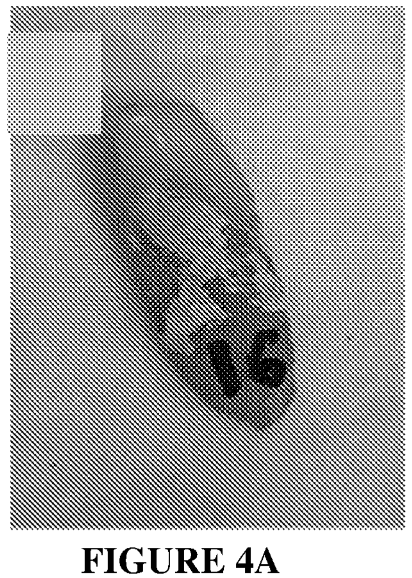
FIGS. 4A-4D presents pictures of teeth with mature tartar before and after treatment with 7.5 mM Si-Urea-Cl NPs (FIG. 4A: before and FIG. 4B: after treatment) and 2 mM of Si-Urea-Cl NPs (FIG. 4C: before and FIG. 4D: after treatment).
Figure 4A:
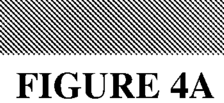
Figure 4B:
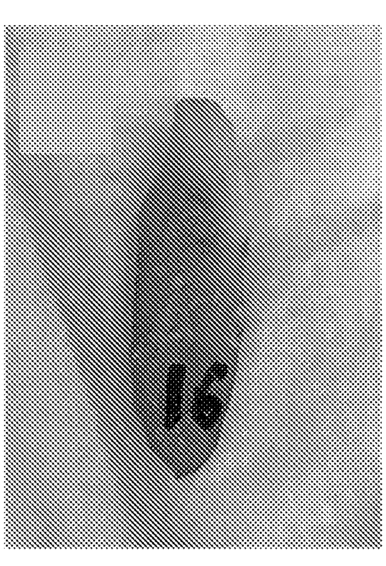
Figure 4C:
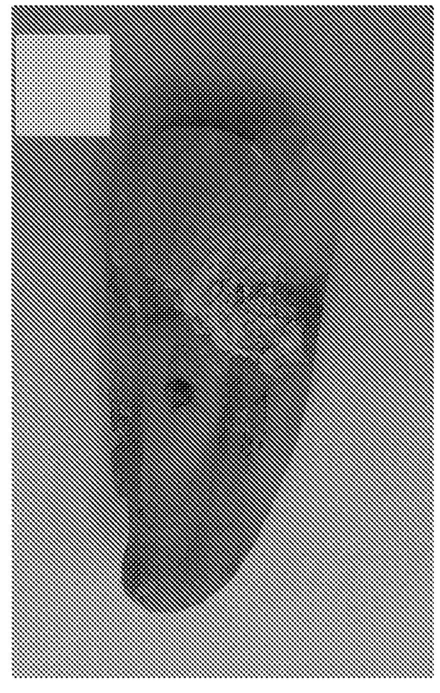
Figure 4D:
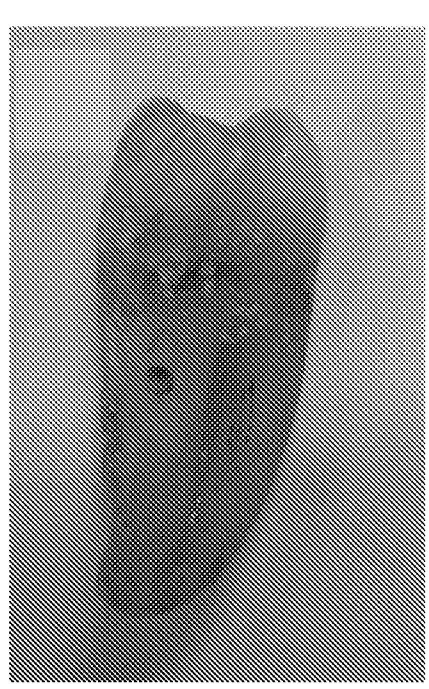
Figure 5A:
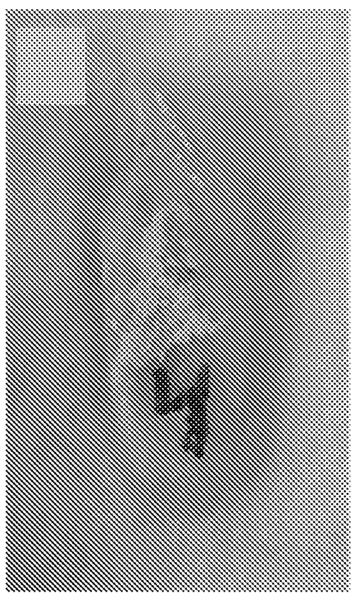
FIGS. 5A-5D presents pictures of teeth with mature tartar before and after treatment with 20 mM of PMAA-Cl (FIG. 5A: before treatment.
Figure 5C:
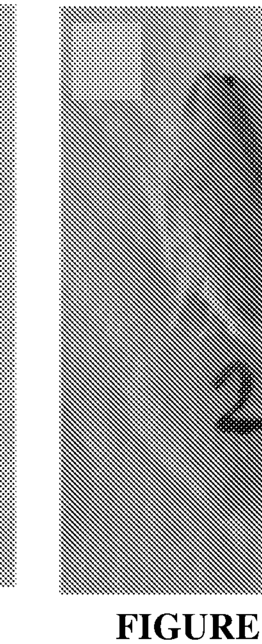
Figure 5B:
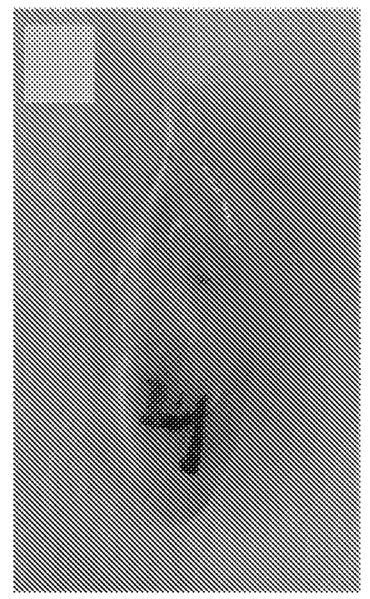
Figure 5B:
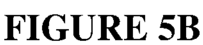
Figure 5D:
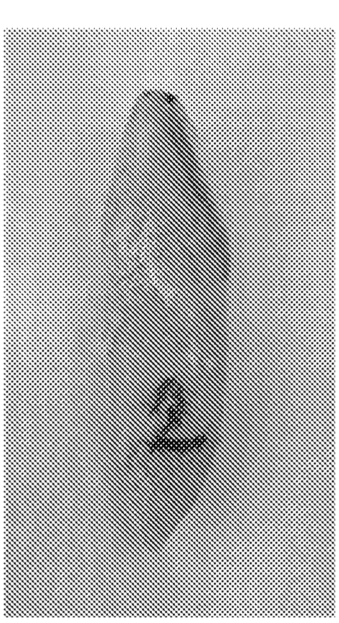

| Sample name | Concentration | pH | Tooth number |
|---|---|---|---|
| DDW | control | 7 | 3 |
| PMAA-Cl NPs (in PBS) - 20 mM | 20 mM (9 mg/mL) | 6-7 | 4 FIG. 5B |
| PMAA-Cl NPs (in PBS) - 2 mM | 2 mM (0.9 mg/mL) | 6-7 | 2 FIG. 5D |
| Si-Urea-Cl NPs - 7.5 mM (as exemplified in Example 6) | 7.5 mM | 6-7 | 16 FIG. 4B |
| Si-Urea-Cl NPs - 2 mM (as exemplified in Example 6) | 2 mM | 6-7 | 15 FIG. 4D |
| SUTP - 10 mg/mL (as exemplified in Example 1) | 10 mg/mL | 3-4 | 1 FIG. 1B |
| SUTP - 1 mg/mL (as exemplified in Example 1) | 1 mg/mL | 3-4 | 10 FIG. 1D |

The activity of PMAA-Cl NPs for removing the tartar from the teeth are presented in FIGS. 5A-5D). The tooth treated with PMAA-Cl NPs at a concentration of 20 mM was completely clean after 10 minutes of stirring and brushing (as shown in FIGS. 5A and 5B). The tooth treated with PMAA-Cl NPs at a lower concentration of 2 mM (FIGS. 5C and 5D) was partially clean and showed a potential for removing the tartar. However, PMAA-Cl NPs at a concentration of 1 mM did not show any effect on the tartar.

The activity of Si-Urea-Cl NPs for removing the tartar from the teeth presented in FIGS. 4A-4D. FIGS. 4A and 4C present the teeth before treatment with Si-Urea NPs. The teeth treated with Si-Urea-C1 NPs at a concentration of 7.5 mM was completely clean after 10 minutes of stirring and brushing (FIG. 4B). A lower concentration of 2 mM did not show a significant effect on the tartar and the tooth was like its initial state (FIG. 4D). It is possible that the lower concertation will be more effective when the stirring time will be longer.

The activity of SUTP for removing the tartar from the teeth are shown in FIGS. 1A-1D. FIGS. 1A, and 1C present the teeth before treatment with SUTP. The tooth treated with SUTP at a concentration of 10 mg/mL (pH 3-4) was completely clean after 10 minutes of stirring and brushing (FIG. 1B). The teeth treated with SUTP at a lower concentration of 1 mg/mL (at pH 3-4 and pH 6-7 (FIG. 1D, respectively) was partially clean, and showed a promising potential for removing the tartar. There was no effect on the tartar when DDW were used (negative control).

Example 9

A comparison of the Activity of Succinyl Tetraphosphonate and Two Types of Industrial Pyrophosphates on Human Teeth The effect of succinyl tetraphosphonate and two types of industrial pyrophosphates on human teeth having mature tartar as were evaluated as followed:

Human teeth were incubated and shaken in 5 ml solution of PBS with SUTP ((a) see structure below), sodium pyrophosphate tetrabasic ((b) see structure below) and sodium pyrophosphate dibasic ((c) see structure below) (1 mg/ml, pH=7) for 10 min. Then, the teeth were brushed by a toothbrush for 2 min. Images were captured before and after treatment FIG. 6 (with SUTP), FIG. 7 (with sodium pyrophosphate tetrabasic), and FIG. 8 (with sodium pyrophosphate dibasic).

(a)

(b)

(c)

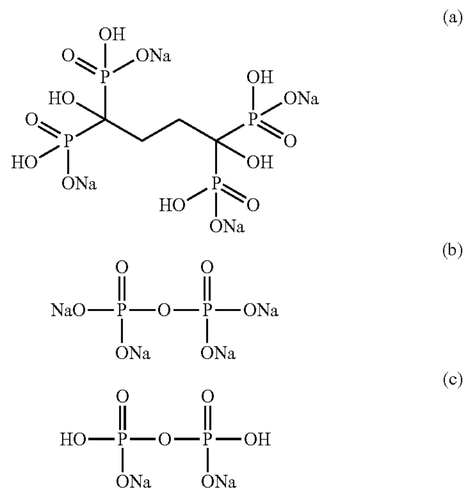

Figure 6:
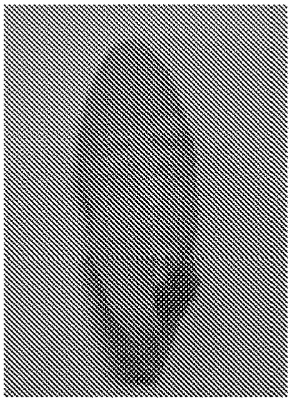
FIG. 6 presents pictures of teeth with mature tartar before and after treatment with succinyl tetra phosphonate (SUTP) at concentration of 1 mg/ml.
Figure 6:
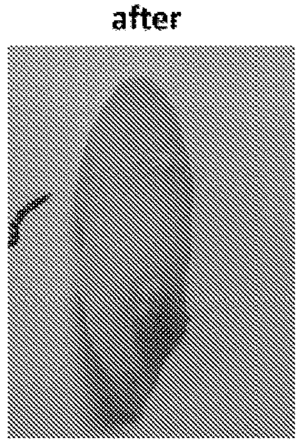
Figure 7:
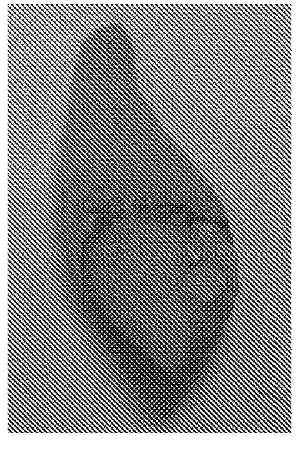
FIG. 7 presents pictures of teeth with mature tartar before and after sodium pyrophosphate tetrabasic treatment with concentration of 1 mg/ml.
Figure 7:
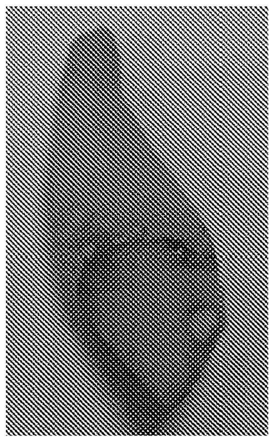
Figure 8:
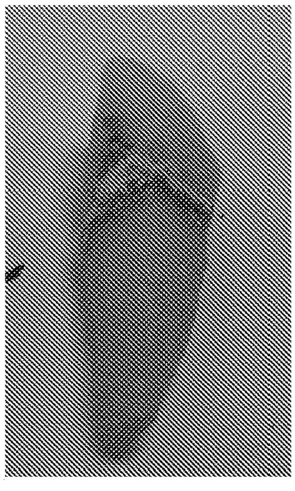
FIG. 8 presents pictures of teeth with mature tartar before and after sodium pyrophosphate dibasic treatment with concentration of 1 mg/ml.
Figure 8:
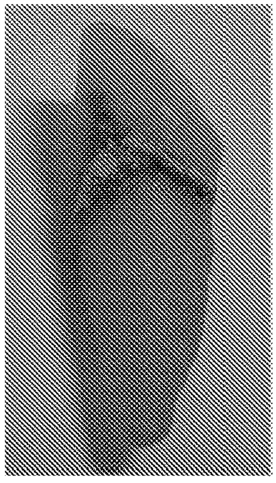

As shown in FIG. 6, a significant mature tartar was removed in SUTP. Sodium pyrophosphate tetrabasic did not remove the mature tartar (FIG. 7). Sodium pyrophosphate dibasic also did not remove the mature tartar (FIG. 8).

Figures 9A, 9B, 9C:
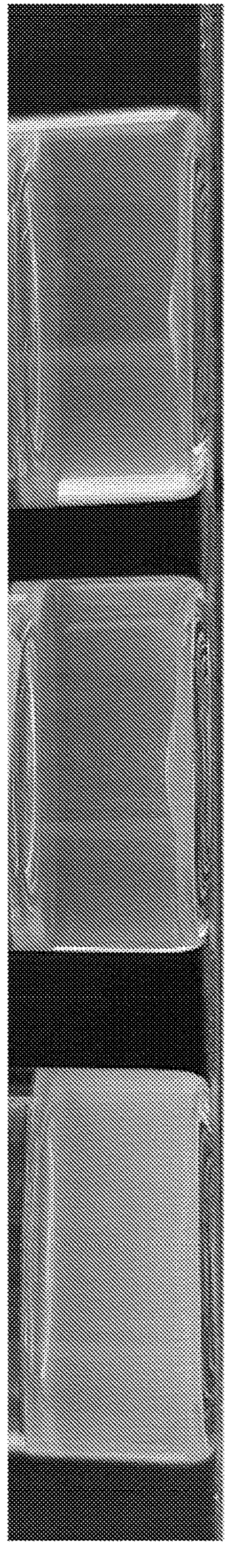
FIGS. 9A-9C presents pictures of three solutions: SUTP solution (FIG. 9A), sodium pyrophosphate dibasic solutions (FIG. 9B) and sodium pyrophosphate tetrabasic solution (FIG. 9C) at a concentration of (1 mg/ml) after the tooth brushing.

In addition, the solutions with concentration 1 mg/ml (FIG. 9) were captured after the teeth brushing, and demonstrated a cloudy solution, but the SUTP solution was significantly cloudier than the others in both concentrations, indicating significantly more tartar that removed from the teeth.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A dental care composition comprising at least one tetra-phosphonate compound or salt thereof, in an amount of 0.05%-30% by weight of said composition; wherein the at least one tetra-phosphonate compound is represented by the following structure:

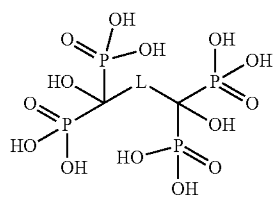

wherein,

L is alkyl, alkylaryl, alkynyl, aryl, alkyl ether, alkyl thioether, alkyl amide, alkyl amine, or an amino side chain; wherein the side chain of the amino acid is attached to the carbon; and wherein said alkyl, alkylaryl, alkynyl, aryl, alkyl ether, alkyl thioether, alkyl amide, alkyl amine, or an amino side chain are each substituted or unsubstituted;

and a pharmaceutically acceptable carrier.

2. The composition according to claim 1, wherein the tetra-phosphonate compound is represented by the following structure:

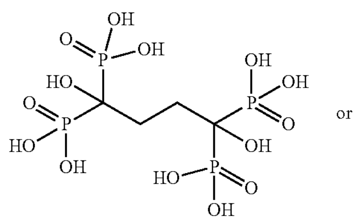

or

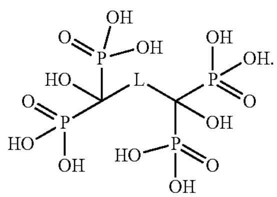

3. The dental care composition of claim 1, wherein the tetra-phosphonate is encapsulated.

4. The dental care composition according to claim 1, wherein the composition further comprises at least one N-halamine compound, N-halamine based polymer, or N-halamine based particle in an amount of between 0.1%-10% by weight of said composition.

5. The dental care composition according to claim 4, wherein the N-halamine compound comprises a halogenated primary amine, a halogenated secondary amine, a halogenated amide or a halogenated urea.

6. The dental care composition according to claim 4, wherein the N-halamine based particle is a nanoparticle or a microparticle.

7. The dental care composition according to claim 4, wherein the N-halamine based particle is in a form of a core/shell silica halamine-urea particles represented by the following structure:

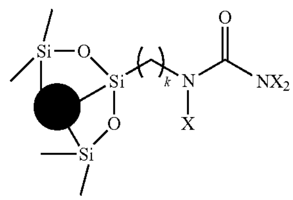

wherein X is independently a halide and k is between 1-10.

8. The dental care composition according to claim 7, wherein the halide is chloride.

9. The dental care composition according to claim 4, wherein the N-halamine polymer is represented by the following structures:

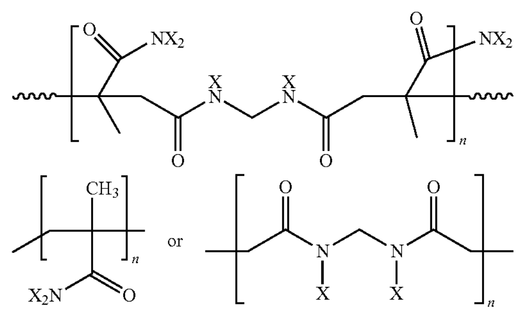

wherein X is independently a halide and n is between 2-100.

10. The dental care composition according to claim 9, wherein the halide is chloride.

11. The dental care composition according to claim 4, wherein the N-halamine compound, N-halamine based polymer, or N-halamine based particle is encapsulated.

12. A method for removing tartar from the tooth surface of a subject by administering/applying a dental care composition according to claim 1.

13. The method according to claim 12, wherein the tartar is mature tartar.

14. A method for removing tartar from the tooth surface of a subject by administering/applying a dental care composition according to claim 4.

15. The method according to claim 14, wherein the tartar is mature tartar.

16. A method for removing mature tartar from the tooth surface of a subject by administering a composition comprising at least one poly-phosphonate or salt thereof, in an amount of 0.05%-30% by weight of said composition; and a pharmaceutically acceptable carrier, wherein the poly-phosphonate compound is a bisphosphonate compound represented by the following structure or salt thereof:

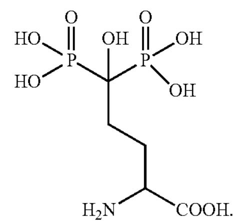 [SMILES: NC(CCC(O)(P(=O)(O)O)P(=O)(O)O)C(=O)O]

or the poly-phosphonate is tetra-phosphonate compound represented by the following structure or salt thereof

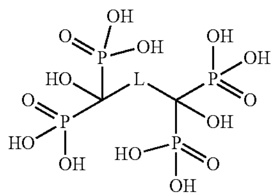

wherein,

L is alkyl, alkylaryl, alkynyl, aryl, alkyl ether, alkyl thioether, alkyl amide, alkyl amine, or an amino side chain; wherein the side chain of the amino acid is attached to the carbon; and wherein said alkyl, alkylaryl, alkynyl, aryl, alkyl ether, alkyl thioether, alkyl amide, alkyl amine, or an amino side chain are each substituted or unsubstituted.

17. The method according to claim 16, wherein the composition further comprises at least one N-halamine compound, N-halamine based polymer, or N-halamine based particle in an amount of between 0.1%-10% by weight of said composition.

18. The method according to claim 17, wherein the N-halamine compound comprises a halogenated primary amine, a halogenated secondary amine, a halogenated amide or a halogenated urea.

19. The method according to claim 17, wherein the N-halamine based particle is a nanoparticle or a microparticle.

20. The method according to claim 17, wherein the N-halamine based particle is in a form of a core/shell silica halamine-urea particles represented by the following structure:

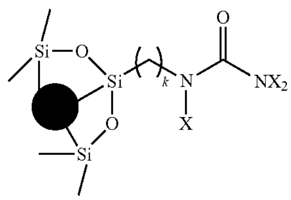

wherein X is independently a halide and k is between 1-10.

21. The method according to claim 17, wherein the N-halamine polymer is represented by the following structures:

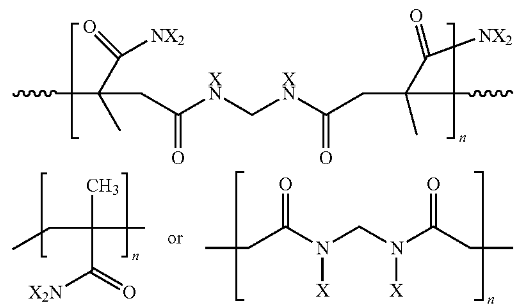

or wherein X is independently a halide and n is between 2-100.

22. The method according to claim 17, wherein the N-halamine based polymer is a nanoparticle or a microparticle.

23. The method according to claim 16, wherein the poly-phosphonate is encapsulated.

24. The method according to claim 17, wherein the N-halamine compound, N-halamine based polymer, or N-halamine based particle is encapsulated.

* * * * *